United States Patent
Loscalzo et al.

(12) 
(10) Patent No.: US 6,589,759 B1
(45) Date of Patent: Jul. 8, 2003

(54) COMPOSITIONS AND METHODS FOR PRODUCING PLATELETS AND/OR PROPLATELETS FROM MEGAKARYOCYTES

(75) Inventors: Joseph Loscalzo, Dover, MA (US); Elisabeth M. Battinelli, Sommerville, MA (US)

(73) Assignee: Trustees of Boston University, Boston, MA (US)

( * ) Notice: Subject to any disclaimer, the term of this patent is extended or adjusted under 35 U.S.C. 154(b) by 0 days.

(21) Appl. No.: 09/937,336

(22) PCT Filed: Mar. 30, 2000

(86) PCT No.: PCT/US00/06436

§ 371 (c)(1), (2), (4) Date: Dec. 5, 2001

(87) PCT Pub. No.: WO00/57891

PCT Pub. Date: Oct. 5, 2000

Related U.S. Application Data

(60) Provisional application No. 60/126,854, filed on Mar. 30, 1999.

(51) Int. Cl.[7] .............................. C12Q 1/34; C12Q 1/56; C12Q 1/00
(52) U.S. Cl. ............................... 435/18; 435/13; 435/2; 435/4; 424/532; 424/529
(58) Field of Search ................................ 435/18, 13, 2, 435/4; 424/532, 529

(56) References Cited

U.S. PATENT DOCUMENTS

| | | | |
|---|---|---|---|
| 5,032,396 A | 7/1991 | Williams | 424/85.2 |
| 5,087,448 A | 2/1992 | Burstein | 424/85.2 |
| 5,128,245 A | 7/1992 | Greenberg et al. | 435/29 |
| 5,155,211 A | 10/1992 | Rosenberg | 530/351 |
| 5,178,856 A | 1/1993 | Burstein | 424/85.2 |
| 5,260,417 A | 11/1993 | Grant et al. | 530/351 |
| 5,326,558 A | 7/1994 | Turner et al. | 424/85.1 |

(List continued on next page.)

FOREIGN PATENT DOCUMENTS

| | | |
|---|---|---|
| WO | WO 96/16645 | 6/1996 |
| WO | WO00/57891 | * 10/2000 |

OTHER PUBLICATIONS

Radomski et al, Br. J. Pharmacol., 107:745–749 (1992).
Battinelli et al, American Heart Association 71st Scientific Sessions, Abstract No. 1400 (Nov. 1998).

(List continued on next page.)

Primary Examiner—Louise N. Leary
(74) Attorney, Agent, or Firm—Hale and Dorr LLP

(57) ABSTRACT

The present invention describes novel compositions and methods to enhance the in vitro and in vivo production of platelets and/or proplatelets from megakaryocytes. The present invention describes compositions comprising megakaryocytes, nitric oxide donors (i.e. compounds that donate, transfer or release nitric oxide, elevate endogenous levels of endothelium-derived relaxing factor, stimulate endogenous synthesis of nitric oxide or are substrates for nitric oxide synthase), and, optionally, at least one thrombopoiesis stimulating factor. The thrombopoiesis stimulating factor is preferably thrombopoietin. The nitric oxide donor is preferable S-nitrosoglutathione. The present invention also describes compositions comprising at least one nitric oxide donor and at least one thrombopoiesis stimulating factor. The present invention also provides methods for treating and/or preventing blood platelet disorders, and for producing platelets and/or proplatelets in vitro and in vivo. The compounds and/or compositions of the present invention can be provided in the form of a pharmaceutical kit.

83 Claims, 2 Drawing Sheets

U.S. PATENT DOCUMENTS

| | | | |
|---|---|---|---|
| 5,427,797 A | 6/1995 | Frostell et al. | 424/434 |
| 5,498,599 A | 3/1996 | Choi et al. | 514/12 |
| 5,498,698 A | 3/1996 | Yamaguchi et al. | 530/399 |
| 5,571,686 A | 11/1996 | Rosenberg et al. | 435/29 |
| 5,593,666 A | 1/1997 | McDonald | 424/85.1 |
| 5,635,387 A | 6/1997 | Fei et al. | 435/378 |
| 5,665,557 A | 9/1997 | Murray et al. | 435/7.24 |
| 5,744,587 A | 4/1998 | Alaska et al. | 530/399 |
| 5,762,920 A | 6/1998 | Yung et al. | 424/85.1 |
| 5,766,581 A | 6/1998 | Bartley et al. | 424/85.1 |
| 5,795,569 A | 8/1998 | Bartley et al. | 424/85.1 |
| 5,834,030 A | 11/1998 | Bolton | 424/613 |
| 5,856,444 A | 1/1999 | Kawakita et al. | 530/350 |
| 5,919,614 A | 7/1999 | Livesey et al. | 435/2 |
| 5,932,546 A | 8/1999 | Barrett et al. | 514/14 |
| 5,977,181 A | 11/1999 | Enikolopov et al. | 514/631 |

OTHER PUBLICATIONS

Battinelli et al, American Heart Association 70th Scientific Sessions, Abstract No. 5946 (Nov. 1997).

Battinelli et al, Graduate Student Science Research Day '99, Boston University, Abstract, Mar. 31, 1999.

Battinelli et al, Fifth Annual Student Achievement Day, Boston University School of Medicine, Abstract, Apr. 7, 1999.

Italiano et al, The Journal of Cell Biology, 147(6):1299–1312 (Dec. 13, 1999).

Radley et al, British Journal of Haematology, 53:277–287 (1983).

Tavassoli et al, Blood Cells, 15:3–14 (1989).

Lelchuk et al, The Journal of Pharmacology and Experimental Therapeutics, 262(3): 1220–1224 (1992).

Zeigler et al, Blood, 84(12):4045–4052 (1994).

Choi et al, Blood, 85(2):402–413 (1995).

Zucker–Franklin et al, Blood, 88(5):1632–1638 (1996).

Ito et al, British Journal of Haematology, 94:387–390 (1996).

Zauli et al, Blood, 90(6):2234–2243 (1997).

Wallerath et al, Thrombosis and Haemostasis, 77(1):163–167 (1997).

Takeuchi et al, British Journal of Haematology, 100:436–444 (1998).

* cited by examiner

COMPOSITIONS AND METHODS FOR PRODUCING PLATELETS AND/OR PROPLATELETS FROM MEGAKARYOCYTES

RELATED APPLICATIONS

This application claims priority to U.S. Provisional Application No. 60/126,854 filed Mar. 30, 1999.

FIELD OF THE INVENTION

The present invention describes in vitro and in vivo production of platelets and/or proplatelets from megakaryocytes. The present invention is also directed to compositions comprising megakaryocytes, nitric oxide donors (i.e. compounds that donate, transfer or release nitric oxide, elevate endogenous levels of endothelium-derived relaxing factor, stimulate endogenous synthesis of nitric oxide or are substrates for nitric oxide synthase), and, optionally, at least one thrombopoiesis stimulating factor. The thrombopoiesis stimulating factor is preferably thrombopoietin. The nitric oxide donor is preferable S-nitrosoglutathione. The present invention also describes compositions comprising at least one nitric oxide donor and at least one thrombopoiesis stimulating factor. The present invention also provides methods for treating and/or preventing blood platelet disorders, and for producing platelets and/or proplatelets in vitro and in vivo. The compounds and/or compositions of the present invention can be provided in the form of a pharmaceutical kit.

BACKGROUND OF THE INVENTION

Platelets are circulating cell derived fragments that are required for the maintenance of hemostasis. These small, anucleate fragments represent the first line of defense against hemorrhage following vascular injury, and are crucial for blood coagulation. Platelets are the terminal differentiation product of megakaryocytes, which in turn originate from pluripotent stem cells. The process of platelet production from megakaryocytes, which is complex and incompletely understood, is called thrombopoiesis. Several cytokines have been reported to stimulate the growth and maturation of megakaryocytes. The interaction between the cytokines and growth factors, their kinetic choreography, and the specific molecular steps that commit the megakaryocytes and their precursors to the process of maturation and platelet production have only begun to be rigorously investigated. Megakaryocytes mature by a process of endomitosis and cytoplasmic maturation. Most research to date has focused on the maturation step of megakaryocyte growth rather than on the terminal process of platelet production.

Morphological studies of marrow megakaryocytes suggest that platelets form as a result of cytoplasmic fragmentation. With the completion of endomitosis, megakaryocyte cytoplasm expands and, in the process, develops demarcation membranes and granules. Platelets form as the fully mature megakaryocyte develops cytoplasmic extensions, or pseudopodial protrusions, that extend in proximity to sinusoidal endothelial cells (Tavassoli and Aoki, *Blood Cells,* 15:3–14, (1989)). Platelets bud from the ends of these protusions and thereafter enter the circulation. The megakaryocyte's ability to produce platelet buds is ultimately exhausted, and it undergoes terminal apoptosis.

The in vitro counterpart to thrombopoiesis is believed to be the development of the "proplatelet" process that has been observed in the terminal phases of megakaryocyte tissue cultures (Choi et al, *Blood,* 85:402–413 (1995)). Some data suggests that proplatelets can produce platelet-like particles (Choi et al, *Blood,* 402–413 (1995); Zeigler et al, *Blood,* 84:4045–4052 (1994)). Proplatelets insinuating between bone marrow sinusoidal cells can enter the circulation (Tavassoli et al, *Blood Cells,* 15:3–14 (1989)). Circulatory shear forces within the marrow or possibly in the pulmonary circulation could result in the fragmentation of these proplatelets, thereby producing platelets in circulation (Burstein et al, Magakaryopoiesis and Platelet Formation, McGraw-Hill, New York, (1995); Trowbridge et al, *Thromb Res.,* 28:461–475 (1982)).

A number of diseases or conditions result from inappropriate levels or inadequate functioning of blood platelets. Platelet disorders are clinically treated by administering thrombopoietin or by whole blood or platelet transfusions. Platelets for such procedures are obtained by plateletphoresis from normal donors; however, blood and platelet supplies can be limited. In addition, platelets have a relatively short shelf-life of about 5 days. Transfusions are also costly and can transmit infections and expose patients to viruses such as the human immunodeficiency virus (HI) or various hepatitis viruses. Furthermore, patients are often refractory to subsequent transfusions. Thrombopoietin treatment has a lag period before the level of platelets are affected and often results in the failure to stimulate platelet production in many patients.

Thus, there remains a need in the art for new and improved methods for in vitro production of platelets for use by patients and for new and improved methods of stimulating or enhancing the production of platelets in vivo, thereby resulting in safer alternatives for treating and/or preventing blood platelet disorders. The present invention is directed to these, as well as other, important ends.

SUMMARY OF THE INVENTION

Nitric oxide (NO) has been shown to mediate a number of actions, including the bactericidal and actions of macrophages and blood vessel relaxation of endothelial cells. NO and NO donors have also been implicated as mediators for a number of processes including vasodilation, neurotransmission, immunity, and vascular and nonvascular smooth muscle relaxation. In the process of arriving at the present invention, it was hypothesized that when the megakaryocytes are committed to platelet production, an endothelial product is released from marrow sinusoidal endothelial cells as they make contact with megakaryocyte protrusions. This endothelium product should promote apoptosis, since platelet formation morphologically resembles programmed cell death (Radley and Hailer, *Br. J. Haematol.,* 53:227–287 (1983)). One possible endothelial product that promotes apoptosis is nitric oxide.

One aspect of the present invention provides compositions comprising at least one megakaryocyte and at least one compound that donates, transfers or releases nitrogen monoxide as a charged species, i.e., nitrosonium ($NO^+$) or nitroxyl ($NO-$), or as the neutral species, nitric oxide ($NO·$), and/or stimulates endogenous production of nitric oxide or endothelium-derived relaxing factor (EDRF) in vivo and/or is a substrate for nitric oxide synthase (i.e., nitric oxide donor). Preferably, the nitric oxide donor is S-nitrosoglutathione. The compositions can comprise a pharmaceutically acceptable carrier. These compositions, which are useful for the in vitro production of platelets and/or proplatelets, can be produced by treating megakaryocytes in culture with an effective amount of at least one nitric oxide donor. These compositions potentiate apoptosis of the cells and increase the number of platelets and/or proplatelets produced.

Another aspect of the present invention provides compositions comprising at least one megakaryocyte, at least one thrombopoiesis stimulating factor, and at least one compound that donates, transfers or releases nitrogen monoxide as a charged species, i.e., nitrosonium ($NO^+$) or nitroxyl (NO-), or as the neutral species, nitric oxide (NO·), and/or stimulates endogenous production of nitric oxide or EDRF in vivo and/or is a substrate for nitric oxide synthase. The thrombopoiesis stimulating factor is preferably thrombopoietin (TPO), and the nitric oxide donor is preferably S-nitroso-glutathione. The compositions can comprise a pharmaceutically acceptable carrier. These compositions, which are useful for the in vitro production of platelets and/or proplatelets, can be produced by treating megakaryocytes in culture with an effective amount of at least one thrombopoiesis stimulating factor and at least one nitric oxide donor. Preferably, the compositions are produced by treating megakaryocytes in culture with an effective amount of at least one thrombopoiesis stimulating factor followed by treatment of the cells with at least one nitric oxide donor. These compositions increase the production of platelets and/or proplatelets in culture.

Another aspect of the present invention provides methods for stimulating the in vivo production of a patient's own platelets and/or proplatelets by administering to a patient a therapeutically effective amount of at least one thrombopoiesis stimulating factor and at least one compound that donates, transfers or releases nitrogen monoxide as a charged species, i.e., nitrosonium ($NO^+$) or nitroxyl (NO-), or as the neutral species, nitric oxide (NO·), and/or stimulates endogenous production of nitric oxide or EDRF in vivo and/or is a substrate for nitric oxide synthase, thereby augmenting the production of the patient's own platelets and/or proplatelets. The thrombopoiesis stimulating factor and nitric oxide donor can be administered separately or as components of the same composition in one or more pharmaceutically acceptable carriers.

Another aspect of the present invention provides methods for treating and/or preventing blood platelet disorders in a patient by administering a therapeutically effective amount of at least one compound that donates, transfers or releases nitrogen monoxide as a charged species, i.e., nitrosonium ($NO^+$) or nitroxyl (NO-), or as the neutral species, nitric oxide (NO·), and/or stimulates endogenous production of nitric oxide or EDRF in vivo and/or is a substrate for nitric oxide synthase, and, optionally, at least one thrombopoiesis stimulating factor. The thrombopoiesis stimulating factor and nitric oxide donor can be administered separately or as components of the same composition in one or more pharmaceutically acceptable carriers. The nitric oxide donor and, optionally, at least one thrombopoiesis stimulating factor can also be administered in combination with other medications for the treatment of blood platelet disorders. These methods of treating and/or preventing platelet disorders are preferable to current transfusion therapies which are vehicles for infections, such as AIDS and hepatitis.

Another aspect of the present invention provides methods for treating and/or preventing blood platelet disorders in a patient by administering platelets and/or proplatelets produced by culturing megakaryocytes in vitro. The megakaryocytes in culture are treated with an effective amount of at least one compound that donates, transfers or releases nitrogen monoxide as a charged species, i.e., nitrosonium ($NO^+$) or nitroxyl (NO-), or as the neutral species, nitric oxide (NO·), and/or stimulates endogenous production of nitric oxide or EDRF in vivo and/or is a substrate for nitric oxide synthase, and, optionally, at least one thrombopoiesis stimulating factor. The thrombopoiesis stimulating factor and nitric oxide donor can be administered separately or as components of the same composition in one or more pharmaceutically acceptable carriers. The megakaryocytes in culture can be derived from a variety of sources, such as cell lines, stem cells, tissues, bone marrow or a patient's own blood megakaryocytic precursors. These methods of treating platelet disorders are preferable to current transfusion therapies which are vehicles for infections, such as AIDS and hepatitis.

Yet another aspect of the present invention provides methods for reducing high platelet counts in a patient by administering an effective amount of at least one compound that inhibits the patient's production of nitric oxide.

These and other aspects of the present invention are described in detail below.

BRIEF DESCRIPTION OF THE FIGURES

FIG. 1A shows an untreated cultured sample of Meg-01 cells positive for GPIHIa. FIG. 1B shows cultured Meg-01 cells treated with 100 $\mu$M S-nitroso-glutathione (SNO-glu) and the formation of GPIIIa positive platelet-sized particle. FIG. 1C shows cultured Meg-01 cells pretreated with 100 ng/ml thrombopoietin, washed with phosphate-buffered saline, and treated with 100 $\mu$M SNO-glu. FIG. 1D shows aggregation of platelet rich fraction with 10 $\mu$M thrombin-receptor activating protein (Trap), 2.5 mM $CaCl_2$, and 600 $\mu$g/ml fibrinogen.

DETAILED DESCRIPTION OF THE INVENTION

Figure 1A:
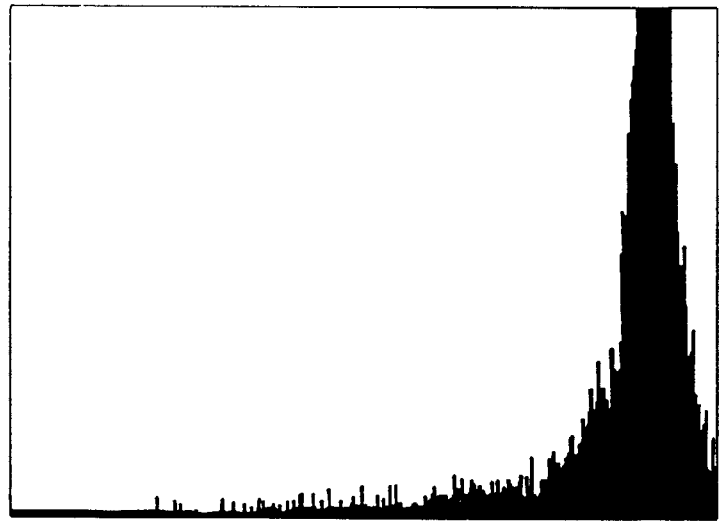
FIGS. 1A–D are flow cytometric analyses of human platelet glycoprotein IIIa (GPIIIa) positive platelet sized particles from Example 1.

As used throughout the disclosure, the following terms, unless otherwise indicated, shall be understood to have the following meanings.

"Patient" refers to animals, preferably mammals, more preferably humans.

"Proplatelets" refer to any structural form of a megakaryocyte or its fragments, such as cytoplasmically-linked platelet-like particles, that could result in platelet formation. The structural forms include, but are not limited to, cells with long cytoplasmic extensions, projections or pseudopodia that contain swellings encompassing platelet bodies in various stages of formation, such as, nodules, blebs, and the like.

"Blood platelet disorder" refers to a condition or disorder caused by blood platelet dysfunction or an insufficient or over supply of blood platelets. Exemplary blood platelet disorders include thrombocytopenia, thrombocythemia and thrombocytopathy.

"Thrombocytopenia" refers to blood platelet disorders characterized by low platelet counts. Exemplary thrombocytopenic platelet disorders are autoimmune, neonatal thrombocytopenia; thrombotic thrombocytopenic purpura; idiopathic (immune) thrombocytopenic purpura; dilutional thrombocytopenia; low platelet count conditions resulting from or associated with aplastic anemia; malignant infiltration; chemotherapy or other bone marrow failure states; bone marrow transplantation; antibody-mediated platelet destruction; blood transfusion; cardiopulmonary by-pass;

AIDS; disseminated intravascular coagulation; hemolytic uremic syndrome; leukemia; hypersplenism; myelodysplastic disorders and arteriovenous realformations; pulmonary hypertension; kidney graft rejection; and administration of heparin or certain other drugs.

"Thrombocythemia" refers to blood platelet disorders characterized by a relatively low platelet count. Exemplary thrombocythemic platelet disorders are idiopathic thrombocythemia and high platelet counts resulting from or associated with reactive thrombocytosis secondary to inflammation; iron deficiency or malignancy, polycythemia vera; chronic myelogenous leukemia; myeloid metaplasia or any other myeloproliferative condition.

"Thrombocytopathy" refers to blood platelet disorders characterized by an abnormally high or low platelet function, although the platelet counts can be in the normal range. Exemplary thrombocytopathic disorders in which the platelet function is low include Mediterranean thrombocytopathy; von Willebrand's disease; and idiopathic (immune) thrombocytopenic purpura. Low platelet function thrombocytopathic conditions can also be associated with or result from HIV infections; drug induced or hereditary storage pool disorders; uremia; and myelodysplastic disorders or thrombolytic therapy. Exemplary thrombocytopathic disorders in which the platelet function is high include thrombocythemia. Thrombocytopathic conditions can also be associated with or result from myeloproliferative disorders; atherosclerosis; myocardial infraction; unstable angina; stroke and other vascular thrombosis disorders such as peripheral vascular disorders and the like.

"Thrombopoiesis stimulating factors" refer to components that are capable of stimulating the growth and maturation of megakaryocytes or hematopoietic stem cells, including cytokines and growth factors. Exemplary thrombopoiesis stimulating factors are interleukins (IL) 1 to 15 (preferably IL-3, IL-6 and IL-11), erythropoietin (EPO), thrombopoietin (TPO), stem cell factors (SCF, also known as mast cell growth factor and c-kit ligand), flt-3 ligand (FL), granulocyte colony stimulating factor (GCSF), granulocyte macrophage colony stimulating factor (GM-CSF), tumor growth factor beta (TGF beta), tumor necrosis factor alpha (TNF alpha), interferon (IFN alpha, beta or gamma), fibroblast growth factor (FGF), platelet-derived growth factor (PDGF), insulin-like growth factors (IGF-1 and IGF-2), leukemia inhibitor factor (LIF), megakaryoctye colony stimulating factor (meg-CSF) and the like. Thrombopoiesis stimulating factors are commercially available, for example, from R&D Systems (Minneapolis, Minn.) or they can be chemically synthesized or isolated by extraction and purification from natural sources, from recombinant cell cultures or recombinant DNA methods. Biologically active equivalents of thrombopoiesis stimulating factors are also effective in stimulating the growth and maturation of megakaryocytes. Biologically active equivalents of thrombopoiesis stimulating factors include, for example, those differing in one or more amino acids in the overall sequence or in the glycosylation pattern; substituted, deleted and/or inserted amino acid variants; and/or post translation modified factors.

"Carriers" or "vehicles" refers to carrier materials suitable for compound administration and include any such material known in the art such as, for example, any liquid, gel, solvent, liquid diluent, solubilizer, or the like, which is non-toxic and which does not interact with any components of the composition in a deleterious manner.

"Nitric oxide adduct" or "NO adduct" refers to compounds and functional groups which, under physiological conditions, can donate, release and/or directly or indirectly transfer any of the three redox forms of nitrogen monoxide ($NO^+$, $NO^-$, $NO\cdot$), such that the biological activity of the nitrogen monoxide species is expressed at the intended site of action.

"Nitric oxide releasing" or "nitric oxide donating" refers to methods of donating, releasing and/or directly or indirectly transferring any of the three redox forms of nitrogen monoxide ($NO^+$, NO–, $NO\cdot$), such that the biological activity of the nitrogen monoxide species is expressed at the intended site of action.

"Nitric oxide donor" or "NO donor" refers to compounds that donate, release and/or directly or indirectly transfer a nitrogen monoxide species, and/or stimulate the endogenous production of nitric oxide or endothelium-derived relaxing factor (EDRF) in vivo and/or elevate endogenous levels of nitric oxide or EDRF in vivo. "NO donor" also includes compounds that are substrates for nitric oxide synthase.

"Alkyl" refers to a lower alkyl group, a haloalkyl group, an alkenyl group, an alkynyl group, a bridged cydoalkyl group, a cycloalkyl group or a heterocyclic ring, as defined herein.

"Lower alkyl" refers to branched or straight chain acyclic alkyl group comprising one to about ten carbon atoms (preferably one to about eight carbon atoms, more preferably one to about six carbon atoms). Exemplary lower alkyl groups include methyl, ethyl, n-propyl, isopropyl, n-butyl, isobutyl, sec-butyl, t-butyl, pentyl, neopentyl, iso-amyl, hexyl, octyl, and the like.

"Haloalkyl" refers to a lower alkyl group, an alkenyl group, an alkynyl group, a bridged cycloalkyl group, a cycloalkyl group or a heterocyclic ring, as defined herein, to which is appended one or more halogens, as defined herein. Exemplary haloalkyl groups include trifluoromethyl, chloromethyl, 2-bromobutyl, 1-bromo-2-chloro-pentyl, and the like.

"Alkenyl" refers to a branched or straight chain $C_2$–$C_{10}$ hydrocarbon (preferably a $C_2$–$C_8$ hydrocarbon, more preferably a $C_2$–$C_6$ hydrocarbon) which can comprise one or more carbon-carbon double bonds. Exemplary alkenyl groups include propylenyl, buten-1-yl, isobutenyl, penten-1-yl, 2,2-methylbuten-1-yl, 3-methylbuten-1-yl, hexan-1-yl, hepten-1-yl, octen-1-yl, and the like.

"Alkynyl" refers to an unsaturated acyclic $C_2$–$C_{10}$ hydrocarbon (preferably a $C_2$–$C_8$ hydrocarbon, more preferably a $C_2$–$C_6$ hydrocarbon) which can comprise one or more carbon-carbon triple bonds. Exemplary alkynyl groups include ethynyl, propynyl, butyn-1-yl, butyn-2-yl, pentyl-1-yl, pentyl-2-yl, 3-methylbutyn-1-yl, hexyl-1-yl, hexyl-2-yl, hexyl-3-yl, 3,3-dimethyl-butyn-1-yl, and the like.

"Bridged cydoalkyl" refers to two or more cycloalkyl groups, heterocyclic groups, or a combination thereof fused via adjacent or non-adjacent atoms. Bridged cydoalkyl groups can be unsubstituted or substituted with one, two or three substituents independently selected from alkyl, alkoxy, amino, alkylamino, dialkylamnino, hydroxy, halo, carboxyl, alkylcarboxylic acid, aryl, amidyl, ester, alkylcarboxylic ester, carboxamido, alkylcarboxamido, oxo and nitro. Exemplary bridged cydoalkyl groups include adamantyl, decahydronapthyl, quinuclidyl, 2,6-dioxabicydo[3.3.0] octane, 7-oxabycyclo[2.2.1]heptyl, 8-azabicyclo[3,2,1]oct-2-enyl and the like.

"Cydoalkyl" refers to a saturated or unsaturated cyclic hydrocarbon comprising from about 3 to about 8 carbon atoms. Cydoalkyl groups can be unsubstituted or substituted with one, two or three substituents independently selected from alkyl, alkoxy, amino, alkylamino, dialkylamino, arylamino, diarylamino, alkylarylamino, aryl, amidyl, ester, hydroxy, halo, carboxyl, alkylcarboxylic acid, alkylcarboxylic ester, carboxamido, alkylcarboxamido, oxo and nitro. Exemplary cycloalkyl groups include cydopropyl, cyclobutyl, cyclopentyl, cydohexyl, cyclohexenyl, cydohepta,1,3ienyl, and the like.

"Heterocyclic ring or group" refers to a saturated, unsaturated, cyclic or aromatic or polycyclic hydrocarbon group having about 3 to about 12 carbon atoms (preferably about 4 to about 6 carbon atoms) where 1 to about 4 carbon atoms are replaced by one or more nitrogen, oxygen and/or sulfur atoms. Sulfur maybe in the thio, sulfinyl or sulfonyl oxidation state. The heterocyclic ring or group can be fused to an aromatic hydrocarbon group. Heterocyclic groups can be unsubstituted or substituted with one, two or three substituents independently selected from alkyl, alkoxy, amino, alkylamino, dialkylamino, arylamino, diarylamino, alkylarylamino, hydroxy, oxo, thial, halo, carboxyl, carboxylic ester, alkylcarboxylic acid, alkylcarboxylic ester, aryl, arylcarboxylic acid, arylcarboxylic ester, amidyl, ester, carboxamido, alkylcarboxamido, arylcarboxamido, sulfonic acid, sulfonic ester, sulfonamido and nitro. Exemplary heterocyclic groups include pyrrolyl, 3-pyrrolinyl,4,5,6-trihydro-2H-pyranyl, pyridinyl, 1,4-dihydropyridinyl, pyrazolyl, triazolyl, pyrimidinyl, pyridazinyl, oxazolyl, thiazolyl, imidazolyl, indolyl, thiophenyl, furanyl, tetrhydrofuranyl, tetrazolyl, 2-pyrrolinyl, 3-pyrrolinyl, pyrrolindinyl, oxazolindinyl 1,3-dioxolanyl, 2,6-dioxabicydo[3,3,0]octanyl, 2-imidazonlinyl, imidazolindinyl, 2-pyrazolinyl, pyrazolidinyl, isoxazolyl, isothiazolyl, 1,2,3-oxadiazolyl, 1,2,3-triazolyl, 1,3,4-thiadiazolyl, 2H-pyranyl, 4H-pyranyl, piperidinyl, 1,4-dioxanyl, morpholinyl, 1,4-dithianyl, thiomorpholinyl, pyrazinyl, piperazinyl, 1,3,5-triazinyl, 1,3,5-trithianyl, benzo(b)thiophenyl, benzimidazolyl, quinolinyl, and the like.

"Heterocyclic compounds" refer to mono- and polycydic compounds comprising at least one aryl or heterocyclic ring.

"Aryl" refers to a monocyclic, bicyclic, carbocyclic or heterocyclic ring system comprising one or two aromatic rings. Exemplary aryl groups include phenyl, pyridyl, napthyl, quinoyl, tetrahydronaphthyl, furanyl, indanyl, indenyl, indoyl, and the like. Aryl groups (including bicylic aryl groups) can be unsubstituted or substituted with one, two or three substituents independently selected from alkyl, alkoxy, amino, alkylamino, dialkylamino, arylamino, diarylamino, alkylarylamino, hydroxy, carboxyl, carboxylic ester, alkylcarboxylic acid, alkylcarboxylic ester, aryl, arylcarboxylic acid, arylcarboxylic ester, alkylcarbonyl, arylcarbonyl, amidyl, ester, carboxamido, alkylcarboxamido, carbomyl, sulfonic acid, sulfonic ester, sulfonamido and nitro. Exemplary substituted aryl groups include tetrafluoro-phenyl, pentafluorophenyl, sulfonamide, alkylsulfonyl, arylsulfonyl, and the like.

"Alkylaryl" refers to an alkyl group, as defined herein, to which is appended an aryl group, as defined herein. Exemplary alkylaryl groups include benzyl, phenylethyl, hydroxybenzyl, fluorobenzyl, fluorophenylethyl, and the like.

"Arylalkyl" refers to an aryl radical, as defined herein, attached to an alkyl radical, as defined herein.

"Cycloalkylalkyl" refers to a cycloalkyl radical, as defined herein, attached to an alkyl radical, as defined herein.

"Heterocyclicalkyl" refers to a heterocyclic ring radical, as defined herein, attached to an alkyl radical, as defined herein.

"Cycloalkenyl" refers to an unsaturated cyclic hydrocarbon having about 3 to about 10 carbon atoms (preferably about 3 to about 8 carbon atoms, more preferably about 3 to about 6 carbon atoms) comprising one or more carbon-carbon double bonds.

"Arylheterocyclic ring" refers to a bi- or tricyclic ring comprised of an aryl ring, as defined herein, appended via two adjacent carbon atoms of the aryl ring to a heterocyclic ring, as defined herein. Exemplary arylheterocyclic rings include dihydroindole, 1,2,3,4-tetra-hydroquinoline, and the like.

"Alkoxy" refers to $R_{50}O-$, wherein $R_{50}$ is an alkyl group, as defined herein. Exemplary alkoxy groups include methoxy, ethoxy, t-butoxy, cyclopentyloxy, and the like.

"Arylalkoxy or alkoxyaryl" refers to an alkoxy group, as defined herein, to which is appended an aryl group, as defined herein. Exemplary arylalkoxy groups indude benzyloxy, phenylethoxy, chlorophenylethoxy, and the like.

"Alkoxyalkyl" refers to an alkoxy group, as defined herein, appended to an alkyl group, as defined herein. Exemplary alkoxyalkyl groups include methoxymethyl, methoxyethyl, isopropoxymethyl, and the like.

"Alkoxyhaloalkyl" refers to an alkoxy group, as defined herein, appended to a haloalkyl group, as defined herein. Exemplary alkoxyhaloalkyl groups include 4-methoxy-2-chlorobutyl and the like.

"Cycloalkoxy" refers to $R_{54}O-$, wherein $R_{54}$ is a cycloalkyl group or a bridged cydoalkyl group, as defined herein. Exemplary cycdoalkoxy groups include cyclopropyloxy, cyclopentyloxy, cyclohexyloxy, and the like.

"Haloalkoxy" refers to a haloalkyl group, as defined herein, to which is appended an alkoxy group, as defined herein. Exemplary haloalkyl groups include 1,1,1-trichloroethoxy, 2-bromobutoxy, and the like.

"Hydroxy" refers to —OH.

"Oxo" refers to =O.

"Oxy" refers to —O $^-R_{77}^+$ wherein $R_{77}$ is an organic or inorganic cation.

"Organic cation" refers to a positively charged organic ion. Exemplary organic cations include alkyl substituted ammonium cations, and the like.

"Inorganic cation" refers to a positively charged metal ion. Exemplary inorganic cations include metal cations such as for example, sodium, potassium, calcium, and the like.

"Hydroxyalkyl" refers to a hydroxy group, as defined herein, appended to an alkyl group, as defined herein.

"Amino" refers to —$NH_2$.

"Nitrate" refers to —O—$NO_2$.

"Nitrite" refers to —O—NO.

"Thionitrate" refers to —S—$NO_2$.

"Thionitrite" and "nitrosothiol" refer to —S—NO.

"Nitro" refers to the group —$NO_2$ and "nitrosated" refers to compounds that have been substituted therewith.

"Nitroso" refers to the group —NO and "nitrosylated" refers to compounds that have been substituted therewith.

"Nitrile" and "cyano" refer to —CN.

"Halogen" or "halo" refers to iodine (I), bromine (Br), chlorine (Cl), and/or fluorine (F).

"Alkylamino" refers to $R\_NH-$, wherein $R\_$ is an alkyl group, as defined herein. Exemplary alkylamino groups include methylamino, ethylamino, butylamino, cydohexylamino, and the like.

"Arylamino" refers to $R_{55}NH-$, wherein $R_{55}$ is an aryl group, as defined herein.

"Dialkylamino" refers to $R_{50}R_{52}N-$, wherein $R_{50}$ and $R_{52}$ are each independently an alkyl group, as defined herein. Exemplary dialkylamino groups include dimethylamino, diethylamino, methyl propargylamino, and the like.

"Diarylamino" refers to $R_{55}R_{60}N$—, wherein $R_{55}$ and $R_{60}$ are each independently an aryl group, as defined herein.

"Alkylarylamino" refers to $R_{50}R_{55}N$—, wherein $R_{50}$ is an alkyl group, as defined herein, and $R_{55}$ is an aryl group, as defined herein.

"Aminoalkyl" refers to an amino group, an alkylamino group, a dialkylamino group, an arylamino group, a diarylamino group, an alkylarylamino group or a heterocyclic ring, as defined herein, to which is appended an alkyl group, as defined herein.

"Aminoaryl" refers to an amino group, an alkylamino group, a dialkylamino group, an arylamino group, a diarylamino group, an alkylarylamino group or a heterocyclic ring, as defined herein, to which is appended an aryl group, as defined herein.

"Thio" refers to —S—.

"Sulfinyl" refers to —S(O)—.

"Methanthial" refers to —C(S)—.

"Thial" refers to =S.

"Sulfonyl" refers to —S(O)$_2$.

"Sulfonic acid" refers to —S(O)$_2$OR$_{76}$, wherein $R_{76}$ is a hydrogen, an organic cation or an inorganic cation.

"Alkylsulfonic acid" refers to a sulfonic acid group, as defined herein, appended to an alkyl group, as defined herein.

"Arylsulfonic acid" refers to an sulfonic acid group, as defined herein, appended to an aryl group, as defined herein "Sulfonic ester" refers to —S(O)$_2$OR$_{58}$, wherein $R_{58}$ is an alkyl group, an aryl group, an alkylaryl group or an aryl heterocyclic ring, as defined herein.

"Sulfonamido" refers to —S(O)$_2$—N(R$_{51}$)(R$_{57}$), wherein $R_{51}$, and $R_{57}$ are each independently a hydrogen atom, an alkyl group, an aryl group, an alkylaryl group, or an arylheterocyclic ring, as defined herein, and $R_{51}$, and $R_{57}$ when taken together are a heterocyclic ring, a cycloalkyl group or a bridged cycloalkyl group, as defined herein.

"Alkylsulfonamido" refers to a sulfonamido group, as defined herein, appended to an alkyl group, as defined herein.

"Arylsulfonamido" refers to a sulfonamido group, as defined herein, appended to an aryl group, as defined herein.

"Alkylthio" refers to $R_{50}S$—, wherein $R_{50}$ is an alkyl group, as defined herein.

"Arylthio" refers to $R_{55}S$—, wherein $R_{55}$ is an aryl group, as defined herein.

"Cycloalkylthio" refers to $R_{54}S$—, wherein $R_{54}$ is a cydoalkyl group or a bridged cycloalkyl group, as defined herein. Exemplary cycloalkylthio groups include cyclopropylthio, cyclopentylthio, cyclohexylthio, and the like.

"Alkylsulfinyl" refers to $R_{50}$—S(O)—, wherein $R_{50}$ is an alkyl group, as defined herein.

"Alkylsulfonyl" refers to $R_{50}$—S(O)$_2$—, wherein $R_{50}$ is an alkyl group, as defined herein.

"Arylsulfinyl" refers to $R_{55}$—S(O)—, wherein $R_{55}$ is an aryl group, as defined herein.

"Arylsulfonyl" refers to $R_{55}$—S(O)$_2$—, wherein $R_{55}$is an aryl group, as defined herein.

"Amidyl" refers to $R_5C(O)N(R_{57})$— wherein $R_{51}$ and $R_{57}$ are each independently a hydrogen atom, an alkyl group, an aryl group, an alkylaryl group, or an aryiheterocydic ring, as defined herein.

"Ester" refers to $R_5C(O)O$— wherein $R_{51}$ is a hydrogen atom, an alkyl group, an aryl group, an alkylaryl group, or an arylheterocycdic ring, as defined herein.

"Carbamoyl" refers to —O—C(O)N(R$_{51}$)(R$_{57}$), wherein $R_{51}$ and $R_{57}$ are each independently a hydrogen atom, an alkyl group, an aryl group, an alkylaryl group or an arylheterocyclic ring, as defined herein, or $R_{51}$ and $R_{57}$ taken together are a heterocyclic ring, a cycloalkyl group or a bridged cydoalkyl group, as defined herein.

"Carbamate" refers to $R_{51}$O—C(O)N(R$_{57}$), wherein $R_{51}$ and $R_{57}$ are each independently a hydrogen atom, an alkyl group, an aryl group, an alkylaryl group or an arylheterocyclic ring, as defined herein, or $R_{51}$ and $R_{57}$ taken together are a heterocydic ring, a cycloalkyl group or a bridged cydoalkyl group, as defined herein.

"Carboxyl" refers to —C(O)OR$_{76}$, wherein $R_{76}$ is a hydrogen, an organic cation or an inorganic cation, as defined herein.

"Carbonyl" refers to —C(O)—.

"Alkylcarbonyl" or "alkanoyl" refers to $R_{50}$—C(O)—, wherein $R_{50}$ is an alkyl group, as defined herein.

"Arylcarbonyl" or "aroyl" refers to $R_{55}$—C(O)—, wherein $R_{55}$ is an aryl group, as defined herein.

"Carboxylic ester" refers to —C(O)OR$_{58}$, wherein $R_{58}$ is an alkyl group, an aryl group, an alkylaryl group or an aryl heterocyclic ring, as defined herein.

"Alkylcarboxylic acid" and "alkylcarboxyl" refer to an alkyl group, as defined herein, appended to a carboxyl group, as defined herein.

"Alkylcarboxylic ester" refers to an alkyl group, as defined herein, appended to a carboxylic ester group, as defined herein.

"Arylcarboxylic acid" refers to an aryl group, as defined herein, appended to a carboxyl group, as defined herein.

"Arylcarboxylic ester" and "arylcarboxyl" refer to an aryl group, as defined herein, appended to a carboxylic ester group, as defined herein.

"Carboxamido" refers to —C(O)N(R$_{51}$)(R$_{57}$), wherein $R_{51}$ and $R_{57}$ are each independently a hydrogen atom, an alkyl group, an aryl group, an alkylaryl group or an arylheterocyclic ring, as defined herein, and $R_{51}$ and $R_{57}$ when taken together with the nitrogen to which they are attached form a heterocyclic ring, a cycloalkyl group or a bridged cycloalkyl group, as defined herein.

"Alkylcarboxamido" refers to an alkyl group, as defined herein, appended to a carboxamido group, as defined herein.

"Arylcarboxamido" refers to an aryl group, as defined herein, appended to a carboxamido group, as defined herein.

"Urea" refers to —N(R$_{59}$)—C(O)N(R$_{51}$)(R$_{57}$) wherein $R_{51}$, $R_{57}$, and $R_{59}$ are each independently a hydrogen atom, an alkyl group, an aryl group, an alkylaryl group, or an arylheterocyclic ring, as defined herein, or $R_{51}$ and $R_{57}$ taken together with the nitrogen to which they are attached form a heterocyclic ring, as defined herein.

"Phosphoryl" refers to —P(R$_{70}$)(R$_{71}$)(R$_{72}$), wherein $R_{70}$ is a lone pair of electrons, sulfur or oxygen, and $R_{71}$ and $R_{72}$ are each independently a covalent bond, a hydrogen, a lower alkyl, an alkoxy, an alkylamino, a hydroxy or an aryl, as defined herein.

The present invention provides methods for treating and/or preventing blood platelet disorders by administering the compositions described herein.

In arriving at the present invention, it was unexpectedly discovered that the administration of one or more nitric oxide donors, and the optional administration of at least one thrombopoiesis stimulating factor, to megakaryocytes, increases the in vitro and in vivo platelet and/or proplatelet production. The stimulation or enhancement of platelet production solely using thrombopoiesis stimulating factors has been previously described. For example, U.S. Pat. No.

5,571,686 describes the use of megapoietin protein for stimulating an increase in the megakaryocyte size and number; U.S. Pat. No. 5,593,666 describes the use of thrombopoietin for increasing platelet cell counts in thrombocytopenia; U.S. Pat. Nos. 5,178,856, 5,087,448 and 5,032,396 describe the use of interleukins to enhance the growth of megakaryocytes or stimulate platelet production; and U.S. Pat. Nos. 5,498,698, 5,498,599 and 5,326,558 describe the use of novel thrombopoiesis stimulating factors (the disclosure of each of these patents are incorporated by reference herein in their entirety). There is no suggestion in the prior art to treat megakaryocytes with a nitric oxide donor alone, or in combination with thrombopoiesis stimulating factors, to increase platelet and/or proplatelet production.

In the present invention, the megakaryocytes for use in vitro and in vivo indude those obtained from any commercially available megakaryocyte-producing cell line, such as, for example, the human megakaryoblastic leukemia cell lines Meg-01 and Meg-01s; cells cultured from any mammalian source such as $CD34^+$ cells from human plasma, $CD34^+CD38-$ hematopoietic cells, human bone marrow $CD34^+$ cells, human fetal liver $CD34^+$ cells, GCSF mobilized peripheral blood $CD34^+$ cells, human embryonic stem cells, and the like; and dones produced from any of the megakaryocytic cell lines using standard doning cell culturing techniques, induding, but not limited to, serial dilution of suspension cells and low density plating of the attached and adhered cells. The megakaryocytes in culture can also include those isolated from a patient's own blood or stem cells or those isolated from tissues such as bone marrow, peripheral blood, liver, fetal liver, and the like.

A principal aspect of the present invention provides novel compositions comprising megakaryocytes in combination with nitric oxide and/or nitric oxide donors. The term "nitric oxide" encompasses uncharged nitric oxide (NO·) and charged nitrogen monoxide species, preferably charged nitrogen monoxide species, such as nitrosonium ion ($NO^+$) and nitroxyl ion ($NO-$). The reactive form of nitric oxide can be provided by gaseous nitric oxide. The nitrogen monoxide releasing, delivering or transferring compounds include any and all such compounds which provide nitrogen monoxide to its intended site of action in a form active for its intended purpose. The term "NO adducts" encompasses any nitrogen monoxide releasing, delivering or transferring compounds, including, for example, S-nitrosothiols, nitrites, nitrates, S-nitrothiols, sydnonimines, 2-hydroxy-2-nitrosohydrazines (NONOates), (E)-alkyl-2-[(E)-hydroxyimino]-5-nitro-3-hexene amines or amides, nitrosoamines, furoxans as well as substrates for the endogenous enzymes which synthesize nitric oxide. The "NO adducts" can be mono-nitrosylated, poly-nitrosylated, mono-nitrosated and/or poly-nitrosated or a combination thereof at a variety of naturally susceptible or artificially provided binding sites for biologically active forms of nitrogen monoxide.

One group of NO adducts is the S-nitrosothiols, which are compounds that include at least one —S—NO group. These compounds include S-nitroso-polypeptides (the term "polypeptide" includes proteins and polyamino acids that do not possess an ascertained biological function, and derivatives thereof); S-nitrosylated amino acids (including natural and synthetic amino acids and their stereoisomers and racemic mixtures and derivatives thereof); S-nitrosylated sugars; S-nitrosylated, modified and unmodified, oligonucleotides (preferably of at least 5, and more preferably 5–200 nucleotides); straight or branched, saturated or unsaturated, aliphatic or aromatic, substituted or unsubstituted S-nitrosylated hydrocarbons; and S-nitroso heterocyclic compounds. S-nitrosothiols and methods for preparing them are described in U.S. Pat. Nos. 5,380,758 and 5,703,073; WO 97/27749; WO 98/19672; and Oae et al, *Org. Prep. Proc. Int.*, 15(3):165–198 (1983), the disclosures of each of which are incorporated by reference herein in their entirety.

Another embodiment of the present invention is S-nitroso amino acids where the nitroso group is linked to a sulfur group of a sulfur-containing amino acid or derivative thereof. Such compounds include, for example, S-nitroso-N-acetylcysteine, S-nitroso-captopril, S-nitroso-N-acetylpenicillamine, S-nitroso-homocysteine, S-nitroso-cysteine and S-nitroso-glutathiorie.

Suitable S-nitrosylated proteins include thiol-containing proteins (where the NO group is attached to one or more sulfur groups on an amino acid or amino acid derivative thereof) from various functional classes including enzymes, such as tissue-type plasminogen activator (TPA) and cathepsin B; transport proteins, such as lipoproteins; heme proteins, such as hemoglobin and serum albumin; and biologically protective proteins, such as immunoglobulins, antibodies and cytokines. Such nitrosylated proteins are described in WO 93/09806, the disclosure of which is incorporated by reference herein in its entirety. Examples include polynitrosylated albumin where one or more thiol or other nucleophilic centers in the protein are modified.

Other examples of suitable S-nitrosothiols include:
(i) $HS(C(R_e)(R_f))_m SNO$;
(ii) $ONS(C(R_e)(R_f))_m R_e$; and
(iii) $H_2N-CH(CO_2H)-(CH_2)_m-C(O)NH-CH(CH_2SNO)-C(O)NH-CH_2-CO_2H$;

wherein m is an integer from 2 to 20; $R_e$ and $R_f$ are each independently a hydrogen, an alkyl, a cycloalkoxy, a halogen, a hydroxy, an hydroxyalkyl, an alkoxyalkyl, an arylheterocyclic ring, an alkylaryl, a cycloalkylalkyl, a heterocyclicalkyl, an alkoxy, a haloalkoxy, an amino, an alkylamino, a dialkylamino, an arylamino, a diarylamino, an alkylarylamino, an alkoxyhaloalkyl, a haloalkoxy, a sulfonic acid, a sulfonic ester, an alkylsulfonic acid, an arylsulfonic acid, an arylalkoxy, an alkylthio, an arylthio, a cydoalkylthio, a cydoalkenyl, a cyano, an aminoalkyl, an aminoaryl, an aryl, an arylalkyl, an alkylaryl, a carboxamido, a alkylcarboxamido, an arylcarboxamnido, an amidyl, a carboxyl, a carbamoyl, a carbamate, an alkylcarboxylic acid, an arylcarboxylic acid, an alkylcarbonyl, an arylcarbonyl, an ester, a carboxylic ester, an alkylcarboxylic ester, an arylcarboxylic ester, a haloalkoxy, a sulfonamido, an alkylsulfonamido, an arylsulfonamido, a sulfonic ester, a urea, a phosphoryl, a nitro, —T—O, or $(C(R_e)(R_f))_k$—T—Q, or $R_e$ and $R_f$ taken together with the carbons to which they are attached form a carbonyl, a methanthial, a heterocyclic ring, a cycloalkyl group or a bridged cydoalkyl group; Q is —NO or —NO$_2$ and T is independently a covalent bond, a carbonyl, an oxygen, —S(O)$_o$— or —N($R_a$)$R_i$—, wherein o is an integer from 0 to 2, $R_a$ is a lone pair of electrons, a hydrogen or an alkyl group; $R_i$ is a hydrogen, an alkyl, an aryl, an alkylcarboxylic acid, an aryl carboxylic acid, an alkylcarboxylic ester, an arylcarboxylic ester, an alkylcarboxamido, an arylcarboxamido, an alkylaryl, an alkylsulfinyl, an alkylsulfonyl, an arylsulfinyl, an arylsulfonyl, a sulfonamido, a carboxamido, a carboxylic ester, an amino alkyl, an amino aryl, —CH$_2$—C(T—Q)($R_e$)($R_f$), or —(N$_2$O$_2^-$)·M$^+$, wherein M$^+$ is an organic or inorganic cation; with the proviso that when $R_i$ is —CH$_2$—C(T—Q)($R_e$)($R_f$) or —(N$_2$O$_2^-$)·M$^+$; then "—T—Q" can be a hydrogen, an alkyl group, an alkoxyalkyl group, an aminoalkyl group, a hydroxy group or an aryl group.

In cases where $R_e$ and $R_f$ are a heterocydic ring or $R_e$ and $R_f$ when taken together with the carbon atoms to which they are attached are a heterocyclic ring, then $R_i$ can be a substituent on any disubstituted nitrogen contained within the radical wherein $R_i$ is as defined herein.

Nitrosothiols can be prepared by various methods of synthesis. In general, the thiol precursor is prepared first, then converted to the S-nitrosothiol derivative by nitrosation of the thiol group with $NaNO_2$ under acidic conditions (pH is about 2.5) which yields the S-nitroso derivative. Acids which can be used for this purpose include aqueous sulfuric, acetic and hydrochloric acids. The thiol precursor can also be nitrosylated by reaction with an organic nitrite such as tert-butyl nitrite, or a nitrosonium salt such as nitrosonium tetraflurorborate in an inert solvent.

Another group of NO adducts for use in the present invention, where the NO adduct is a compound that donates, transfers or releases nitric oxide, include compounds comprising at least one ON—O—, ON—N— or ON—C— group. The compounds that include at least one ON—O—, ON—N— or ON—C— group are preferably ON—O—, ON—N— or ON—C-polypeptides (the term "polypeptide" includes proteins and polyamino acids that do not possess an ascertained biological function, and derivatives thereof); ON—O, ON—N— or ON—C-amino acids (including natural and synthetic amino acids and their stereoisomers and racemic mixtures); ON—O—, ON—N— or ON—C-sugars; ON—O—, ON—N— or ON—C— modified or unmodified oligonudeotides (comprising at least 5 nucleotides, preferably 5–200 nucleotides); ON—O—, ON—N— or ON—C— straight or branched, saturated or unsaturated, aliphatic or aromatic, substituted or unsubstituted hydrocarbons; and ON—O—, ON—N— or ON—C— heterocyclic compounds.

Another group of NO adducts for use in the present invention include nitrates that donate, transfer or release nitric oxide, such as compounds comprising at least one $O_2N$—O—, $O_2N$—N—, $O_2N$—S— or $O_2N$—C— group. Preferred among these compounds are $O_2N$—O—, $O_2N$—N—, $O_2N$—S— or $O_2N$—C— polypeptides (the term "polypeptide" includes proteins and also polyamino acids that do not possess an ascertained biological function, and derivatives thereof); $O_2N$—O—, $O_2N$—N—, $O_2N$—S— or $O_2N$—C— amino acids (including natural and synthetic amino acids and their stereoisomers and racemic mixtures); $O_2N$—O—, $O_2N$—N—, $O_2N$—S— or $O_2N$—C-sugars; $O_2N$—O—, $O_2N$—N—, $O_2N$—S— or $O_2N$—C— modified and unmodified oligonucleotides (comprising at least 5 nucleotides, preferably 5–200 nucleotides); $O_2N$—O—, $O_2N$—N—, $O_2N$—S— or $O_2N$—C— straight or branched, saturated or unsaturated, aliphatic or aromatic, substituted or unsubstituted hydrocarbons; and $O_2N$—O—, $O_2N$—N—, $O_2N$—S— or $O_2N$—C— heterocyclic compounds. Preferred examples of compounds comprising at least one $O_2N$—O—, $O_2N$—N—, $O_2N$—S— or $O_2N$—C— group include isosorbide dinitrate, isosorbide mononitrate, clonitrate, erythrityltetranitrate, mannitol hexanitrate, nitroglycerin, pentaerythritol-tetranitrate, pentrinitrol and propatylnitrate.

Another group of NO adducts are N-oxo-N-nitrosoamines that donate, transfer or release nitric oxide and are represented by the formula: $R^1R^2$—N(O— $M^+$)—NO, where $R^1$ and $R^2$ are each independently a polypeptide, an amino acid, a sugar, a modified or unmodified oligonucleotide, a straight or branched, saturated or unsaturated, aliphatic or aromatic, substituted or unsubstituted hydrocarbon, or a heterocylic group, and $M^{30}$ is as defined herein.

Another group of NO adducts are thionitrates that donate, transfer or release nitric oxide and are represented by the formula: $R^1$—(S)—$NO_2$, where $R^1$ is a polypeptide, an amino acid, a sugar, a modified or unmodified oligonucleotide, a straight or branched, saturated or unsaturated, aliphatic or aromatic, substituted or unsubstituted hydrocarbon, or a heterocyclic group. Preferred are those compounds where $R^1$ is a polypeptide or hydrocarbon with a pair or pairs of thiols that are sufficiently structurally proximate, i.e., vicinal, that the pair of thiols will be reduced to a disulfide. Compounds which form disulfide species release nitroxyl ion (NO–) and uncharged nitric oxide (NO·).

The present invention is also directed to compounds that stimulate endogenous NO or elevate levels of endogenous endothelium-derived relaxing factor (EDRF) in vivo or are substrates for the enzyme, nitric oxide synthase. Such compounds include, for example, L-arginine, L-homoarginine, and N-hydroxy-L-arginine, including their nitrosated and nitrosylated analogs (e.g., nitrosated L-arginine, nitrosylated L-arginine, nitrosated N-hydroxy-L-arginine, nitrosylated N-hydroxy-L-arginine, nitrosated L-homoarginine and nitrosylated L-homoarginine), precursors of L-arginine and/or physiologically acceptable salts thereof, including, for example, citrulline, ornithine, glutamine, lysine, polypeptides comprising at least one of these amino acids, inhibitors of the enzyme arginase (e.g., N-hydroxy-L-arginine and 2(S)-amino-6-oronohexanoic acid), and the substrates for nitric oxide synthase, cytokines, adenosin, bradykinin, calreticulin, bisacodyl, and phenolphthalein. EDRF is a vascular relaxing factor secreted by the endothelium, and has been identified as nitric oxide (NO) or a closely related derivative thereof (Palmer et al, *Nature*, 327:524–526 (1987); Ignarro et al, *Proc. Natl. Acad. Sci. USA*, 84:9265–9269 (1987)).

Compounds of the present invention which have one or more asymmetric carbon atoms may exist as the optically pure enantiomers, pure diastereomers, mixtures of enantiomers, mixtures of diastereomers, racemic mixtures of enantiomers, diastereomeric racemates or mixtures of diastereomeric racemates. It is to be understood that the present invention anticipates and includes within its scope all such isomers and mixtures thereof.

Another embodiment of the present invention describes compositions comprising megakaryocytes, at least one thrombopoiesis stimulating factor in combination with at least one nitric oxide donor. These compositions enhance the platelet and/or proplatelet production from megakaryocytes in culture or in vivo. The thrombopoiesis stimulating factor can be any described herein or otherwise known in the art, and is preferably thrombopoietin, interleukin 3, interleukin 6 or interleukin 11, Flt 3, stem cell factors, or mixtures thereof; and is more preferably thrombopoietin (TPO).

The present invention also provides methods for treating and/or preventing blood platelet disorders in a patient by administering to the patient a therapeutically effective amount of at least one nitric oxide donor in combination with at least one thrombopoiesis stimulating factor. This method enhances the growth and production of the patient's own platelets. The compounds can be administered separately or as components of the same composition. The compounds of the present invention can also be administered in combination with other medications used for the treatment of platelet disorders. These medications include but are not limited to corticosteroids (such as, for example, dexamethasone, prednisone including those corticosteroids described in the art, for example, in Goodman and Gilman, The Pharmacological Basis of Therapeutics (9th Ed.), McGraw-Hill, Inc. (1996), the Merck Index on CD-ROM, Twelfth Edition, Version 12:1, (1996), STN Express, file phar and file registry), and immunoglobulins (such as, for example, immunoglobulin G). The treatment of thrombocytopenia using corticosteroids and/or immunoglobulins has been previously described. For example, Dunst et al, *Am J. Kidney Dis.*, 31(1):116–120 (1998) describes the use of corticosteroids for the treatment of thrombocytopenia; Hocker-Schulz et al, *Klin. Padiatr.*, 209(1):30–35 (1997) describes the use of corticosteroids and immunoglobulins for the treatment of acute and chronic immune thrombocytopenia in childhood; Imbach et al, *Lancet*, 2(8453): 464–468 (1985) conducts a multicenter study comparing the effect of immunoglobulin versus corticosteroids for the treatment of thrombocytopenic purpura (the disclosure of each of these are incorporated by reference herein in their entirety). The ability to enhance the production of a patient's own platelets eliminates the need for platelet transfusions, which carry the possibility of transmission of many bloodborn infectious diseases.

There has been an increase in the number of platelet transfusions being performed. This increase appears to be due to the advances in medical technology and to greater access to such technologies as cardiac surgery and bone marrow, heart and liver transplants. Platelet transfusion is also used to hasten the recovery of the platelet counts in those patients whose megakaryocytes have been suppressed by chemotherapy or radiation for malignant diseases.

Another aspect of the present invention provides methods for treating and/or preventing blood platelet disorders in a patient by administering a therapeutically effective amount of platelets and/or proplatelets produced in vitro from megakaryocytes in culture by administration of at least one nitric oxide donor, and, optionally, at least one thrombopoiesis stimulating factor.

Yet another aspect of the present invention provides methods for decreasing the platelet counts in a patient by administering an effective amount of at least one compound that inhibits the production of the patient's own nitric oxide. Such compounds include inhibitors of nitric oxide synthase (NOS) such as, for example, $N^G$-nitro-L-arginine, $N^G$-amino-L-arginine, $N^G$—$N^G$-dmethyl-arginine and $N^G$-mono-methyl-L-arginine, and the like.

For producing platelets and/or proplatelets in vitro, an effective amount of at least one nitric oxide donor (i.e., at least one compound that donates, transfers, or releases nitric oxide, or induces the production of endogenous nitric oxide or endothelium-derived relaxing factor or is a substrate for nitric oxide synthase or a pharmaceutically acceptable salt thereof) is added to at least one megakaryocyte. In other in vitro embodiments, an effective amount of at least one nitric oxide donor and at least one thrombopoiesis stimulating factor are added to the at least one megakaryocyte, where the at least one nitric oxide donor and the at least one thrombopoiesis stimulating factor are added separately to the at least one megakaryocyte or are in the form of a composition when they are added to the at least one megakaryocyte. In other alternative in vitro embodiments, the at least one nitric oxide donor can be added to the at least one megakaryocyte simultaneously with, subsequent to, or prior to adding the at least one thrombopoiesis stimulating factor to the at least one megakaryocyte. In preferred in vitro embodiments for producing platelets and/or proplatelets, at least one thrombopoiesis stimulating factor is added to at least one megakaryocyte, and subsequently at least one nitric oxide donor is added to the at least one megakaryocyte and the at least one thrombopoiesis stimulating factor. As one skilled in the art will recognize from the description herein, after the platelets and/or proplatelets are produced in vitro following the methods described herein, they can then be administered in a therapeutically effective amount to a patient to treat or prevent a blood platelet disorder.

When administered in vivo, the compositions of the present invention can be administered alone or in combination with pharmaceutically acceptable carriers or diluents and in dosages described herein using methods that allow access to the patient's blood stream and that allow contact with the patient's megakaryocytes. When at least one thrombopoiesis stimulating factor and at least one nitric oxide donor are administered together in the form of a composition, they can also be used in combination with one or more additional compounds. Alternatively, the nitric oxide donor(s) can be administered simultaneously with, subsequently to, or prior to administration of the thrombopoiesis stimulating factor(s) and/or other additional compound(s). The preferred method of administration of the nitric oxide donor is subsequent to the administration of the thrombopoiesis stimulating factor.

The dosage regimen for treating and/or preventing blood platelet disorders with the compounds and/or compositions of the present invention is selected in accordance with a variety of factors, including the age, weight, sex, diet and medical condition of the patient, the severity of the disease, the route of administration, pharmacological considerations such as the activity, efficacy, pharmacokinetic and toxicology profiles of the particular compound used, whether a drug delivery system is used and whether the compound is administered as part of a drug combination. Thus, the dosage regimen actually used can vary widely and therefore can deviate from the preferred dosage regimen set forth herein.

The compounds and compositions of the present invention can be administered by any available and effective delivery system including, but not limited to, orally, bucally, parenterally, by inhalation spray, by topical application, by injection, by transurethral drug delivery, transdermally, or rectally (e.g., by the use of suppositories) in dosage unit formulations containing conventional nontoxic pharmaceutically acceptable carriers, adjuvants, and vehicles, as desired. Parenteral includes subcutaneous injections, intravenous injections, intramuscular injections, intrasternal injections, and infusion techniques. Parenteral also includes injection, which can be conducted using any effective injection system including, but not limited to, conventional syringe-and-needle systems or needleless injection devices.

Transdermal drug administration, which is known to one skilled in the art, involves the delivery of pharmaceutical agents via percutaneous passage of the drug into the systemic circulation of the patient. Topical administration, which is well known to one skilled in the art, involves the delivery of pharmaceutical agents via percutaneous passage of the drug into the systemic circulation of the patient. Topical administration can also involve transdermal patches or iontophoresis devices. Other components can be incorporated into the transdermal patches as well. For example, compositions and/or transdermal patches can be formulated with one or more preservatives or bacteriostatic agents including, but not limited to, methyl hydroxybenzoate, propyl hydroxybenzoate, chlorocresol, benzalkonium chloride, and the like.

Dosage forms for topical administration of the compounds and compositions of the present invention preferably include creams, sprays, lotions, gels, ointments, emulsions, liposomes, foams, and the like. Administration of the cream, spray, lotion, gel, ointment, emulsion, coating, liposome, or foam can be accompanied by the use of an applicator for drug delivery using a syringe with or without a needle, and is within the skill of the art.

Solid dosage forms for oral administration can include capsules, tablets, effervescent tablets, chewable tablets, pills, powders, effervescent powders, sachets, granules and gels. In such solid dosage forms, the active compounds can be admixed with at least one inert diluent such as sucrose, lactose or starch. Such dosage forms can also comprise, as in normal practice, additional substances other than inert diluents, e.g., lubricating agents such as magnesium stearate. In the case of capsules, tablets, effervescent tablets, and pills, the dosage forms can also comprise buffering agents. Soft gelatin capsules can be prepared to contain a mixture of the active compounds or compositions of the present invention and vegetable oil. Hard gelatin capsules can contain granules of the active compound in combination with a solid, pulverulent carrier such as lactose, saccharose, sorbitol, mannitol, potato starch, corn starch, amylopectin, cellulose derivatives of gelatin. Tablets and pills can be prepared with enteric coatings.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting agents, emulsifying and suspending agents, and sweetening, flavoring, and perfuming agents.

Suppositories for administration of the compounds and compositions of the invention can be prepared by mixing the compounds or compositions with a suitable nonirritating excipient such as cocoa butter and polyethylene glycols which are solid at room temperature but liquid at body temperature, such that they will melt and release the drug.

Injectable preparations, for example, sterile injectable aqueous or oleaginous suspensions can be formulated according to the known art using suitable dispersing agents, wetting agents and/or suspending agents. The sterile injectable preparation can also be a sterile injectable solution or suspension in a nontoxic parenterally acceptable diluent or solvent, for example, as a solution in 1,3-butanediol. Among the acceptable vehicles and solvents that can be used are water, Ringer's solution, and isotonic sodium chloride solution. Sterile fixed oils are also conventionally used as a solvent or suspending medium.

The compounds and compositions of the present invention will typically be administered in a pharmaceutical composition containing one or more carriers or excipients, i.e., pharmaceutically acceptable organic or inorganic carrier substances suitable for parenteral application which do not deleteriously react with the active compounds. Examples of pharmaceutically acceptable carriers include, for example, water, salt solutions, alcohol, silicone, waxes, petroleum jelly, vegetable oils, polyethylene glycols, propylene glycol, liposomes, sugars, gelatin, lactose, amylose, magnesium stearate, talc, surfactants, silicic acid, viscous paraffin, perfume oil, fatty acid monoglycerides and diglycerides, petroethral fatty acid esters, hydroxymethyl-cellulose, polyvinylpyrrolidone, and the like. The compositions can also include one or more permeation enhancers including, for example, dimethylsulfoxide (DMSO), dimethyl formamide (DMF), N,N-dimethylacetamide (DMA), decylmethylsulfoxide (ClOMSO), polyethylene glycol monolaurate (PEGML), glyceral monolaurate, lecithin, 1-substituted azacycloheptan-2-ones, particularly 1-N-dodecylcyclazacylcoheptan-2-ones (available under the trademark AZONE™ from Nelson Research & Development Co., Irvine, Calif.), alcohols and the like.

The pharmaceutical preparations can be sterilized and if desired, rnrxed with auxiliary agents which do not deleteriously react with the active compounds, e.g., lubricants, preservatives, stabilizers, wetting agents, emulsifiers, salts for influencing osmotic pressure, buffers, colorings, flavoring and/or aromatic substances, and the like. For parenteral application, particularly suitable vehicles consist of solutions, preferably oily or aqueous solutions, as well as suspensions, emulsions, or implants. Aqueous suspensions may contain substances which increase the viscosity of the suspension and include, for example, sodium carboxymethyl cellulose, sorbitol and/or dextran. Optionally, the suspension may also contain stabilizers.

The composition, if desired, can also contain minor amounts of wetting agents, emulsifying agents and/or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulations can include standard carriers such as pharmaceutical grades of mannitol, lactose, starch, magnesium stearate, sodium saccharine, cellulose, magnesium carbonate, and the like.

Various delivery systems are known and can be used to administer the compounds or compositions of the present invention, including, for example, encapsulation in liposomes, microbubbles, emulsions, micropartides, microcapsules and the like. The required dosage can be administered as a single unit or in a sustained release form.

The bioavailability of the compositions can be enhanced by micronization of the formulations using conventional techniques such as grinding, milling, spray drying and the like in the presence of suitable excipients or agents such as phospholipids or surfactants.

The compounds and compositions of the present invention can be formulated as pharmaceutically acceptable salts. Pharmaceutically acceptable salts include, for example, alkali metal salts and addition salts of free acids or free bases. The nature of the salt is not critical, provided that it is pharmaceutically-acceptable. Suitable pharmaceutically-acceptable acid addition salts may be prepared from an inorganic acid or from an organic acid. Examples of such inorganic acids include, but are not limited to, hydrochloric, hydrobrornic, hydroiodic, nitric (nitrate salt), nitrous (nitrite salt), carbonic, sulfuric and phosphoric acid and the like. Appropriate organic acids include, but are not limited to, aliphatic, cycloaliphatic, aromatic, heterocyclic, carboxylic and sulfonic classes of organic acids, such as, for example, formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethane-sulfonic, sulfanilic, stearic, algenic, hydroxy-butyric, cyclohexylaminosulfonic, galactaric and galacturonic acid and the like. Suitable pharmaceutically-acceptable base addition salts include, but are not limited to, metallic salts made from aluminum, calcium, lithium, magnesium, potassium, sodium and zinc or organic salts made from primary, secondary and tertiary amines, cyclic amines, N,N'-dibenzylethylenediamine, chloroprocaine, choline, diethanolamine, ethylenediamine, meglumine (N-methylglucamine) and procaine and the like. All of these salts may be prepared by conventional means from the corresponding compound by reacting, for example, the appropriate acid or base with the compound.

"Therapeutically effective amount" refers to the amount of the nitric oxide donor and/or thrombopoiesis stimulating factor which is effective to achieve its intended purpose by allowing access into a patient's blood stream and enable contact with the patient's own megakaryocytes. "Therapeutically effective amount" also refers to the amount of platelets and/or proplatelets necessary to prevent or treat a blood disorder as described herein. While individual patient needs may vary, determination of optimal ranges for effective amounts of each nitric oxide adduct is within the skill of the art. Generally the dosage regimen for treating a condition with the compounds and/or compositions of this invention is selected in accordance with a variety of factors, including the type, age, weight, sex, diet and medical condition of the patient, the severity of the dysfunction, the route of administration, pharmacological considerations such as the activity, efficacy, pharmacokinetic and toxicology profiles of the particular compound used, whether a drug delivery system is used, and whether the compound is administered as part of a drug combination and can be adjusted by one skilled in the art. Thus, the dosage regimen actually employed may vary widely and therefore may deviate from the preferred dosage regimen set forth herein.

A particularly preferred method of administering the thrombopoiesis stimulating factor and the nitric oxide donor is intravenously. If desired the compounds and/or compositions can be administered subcutaneously. When systemically administered, the therapeutic compositions are in the form of pyrogen-free, parenterally acceptable aqueous solutions.

The present invention also provides pharmaceutical kits comprising one or more containers filled with one or more of the ingredients of the pharmaceutical compounds and/or compositions of the present invention, including, at least, one or more thrombopoiesis stimulating factors in combination with one or more of the NO donors described herein. Such kits can also include, for example, other compounds and/or compositions (e.g., antibiotics), a device(s) for administering the compounds and/or compositions, and written instructions in a form prescribed by a governmental agency regulating the manufacture, use or sale of pharmaceuticals or biological products, which instructions can also reflects approval by the agency of manufacture, use or sale for human administration.

EXAMPLES

The invention is further demonstrated in the following examples. The examples are for purposes of illustration only, and are not intended to limit the scope of the present invention or claims.

As described in Example 1 herein, treatment of megakaryocyte cell line, Meg-01 cells, with the thrombopoiesis stimulating factor TPO, followed by the nitric oxide donor S-nitroso-glutathione (SNO-glu), promoted platelet-like particle formation by the megakaryocytes relative to the cells that were not treated with SNO-glu. The increase in the production of the platelet-like particles was determined by flow cytometry. The platelet-like particles were found to be functional, to express activated glycoprotein IIb/IIIa on their surface in response to thrombin-receptor activating peptide, and to form aggregates when activated in the presence of calcium and fibrinogen. As described in Example 2, these cells were shown to produce CGMP thereby suggesting that nitric oxide might be involved in the process as it is known that cGMP is elevated by nitric oxide. Additionally mice in which the iNOS gene has been deleted have one-half the platelet counts of wild type mice, supporting the importance of endogenous nitric oxide in thrombopoiesis (Table 2).

Example 1

Platelet Production from Megakaryocytes

The production of platelet-sized particles in the Meg-01 cell line using flow cytometry was determined. Human megakaryoblastic leukemia cell line Meg-01 was obtained from American Type Culture Collection (Manassas, Va.) and grown in phenol red-free RPMI-1640 media (Gibco-BRL, Grand Island, N.Y.) supplemented with 10% fetal bovine serum at 37° C. in a humidified atmosphere of 5% $CO_2$. The experiment to monitor platelet production by the megakaryocytoid cell line, Meg-01, were performed as follows: 10 ml of Meg-01 cells ($1\times10^5$/ml) were treated with 100 ng/ml of thrombopoietin (TPO, Amgen, Thousand Oaks, Calif.) for 72 hours. The cells were then centrifuged at 1000 rpm for 10 minutes, washed with phosphate buffered saline (PBS) and resuspended in RPMI-1640 media. Meg-01 cells, in the presence and absence of TPO, were treated with 100 $\mu$M SNO-glu for 2 hours. The cells were collected by centrifugation (1000 rpm for 10 minutes), washed once in PBS, resuspended in 500 $\mu$l of 3% formaldehyde, and allowed to fix for 20 minutes at room temperature. After fixation, 100 $\mu$l of cells were labeled with fluorescein isothiocyanate-conjugated (FITC)-conjugated monoclonal mouse anti-human platelet glycoprotein IIIa, CD61 (GPIIIa, DAKO Corp. Carpinteria, Calif.) at a near saturating concentration and incubated at room temperature for 20 minutes. The sample was diluted in 100 $\mu$l of PBS and analyzed on a Coulter EPICS XL flow cytometer (Coulter, Miami, Fla.). DNA check flow cytometry beads purchased from Coulter were used for daily instrument calibration. Appropriate color compensation was set for FITC fluorescence and phycoerythrin fluorescence using 525 nm and 575 nm band pass filters, respectively. All data were saved in flow cytometry list mode files and analyzed using Coulter ELITE software, version 2.21. Platelet-sized particles were identified by characteristic log forward light scatter (LFS). Only those particles that bound the anti-GPIIIa-FITC antibody (CD41 FITC-conjugated antibody) (Dako, Denmark) were analyzed (by gating the fluorescence signal).

FIG. 1A is the flow cytometric analysis of untreated, cultured samples of Meg-01 cells positive for GPIIIa.

Figure 1B:
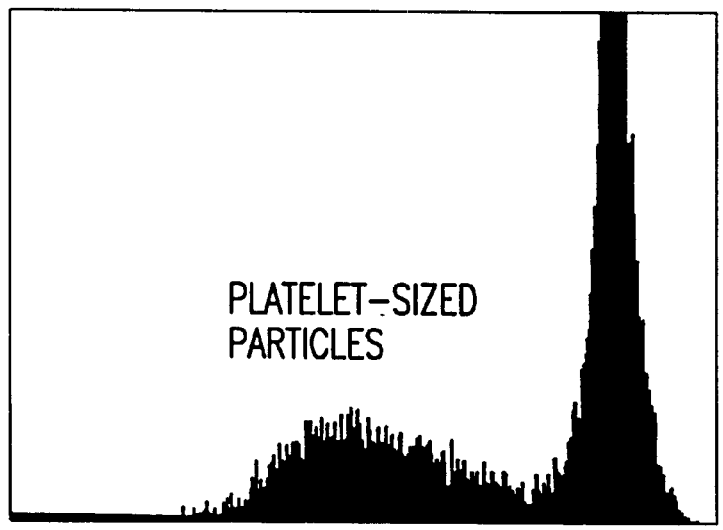

FIG. 1B shows that Meg-01 cells treated with 100 $\mu$M S-nitroso-glutathione (SNO-glu) show the formation of GPIIIa positive platelet-sized particle population in addition to GPIIIa positive Meg-01 cells.

Figure 1C:
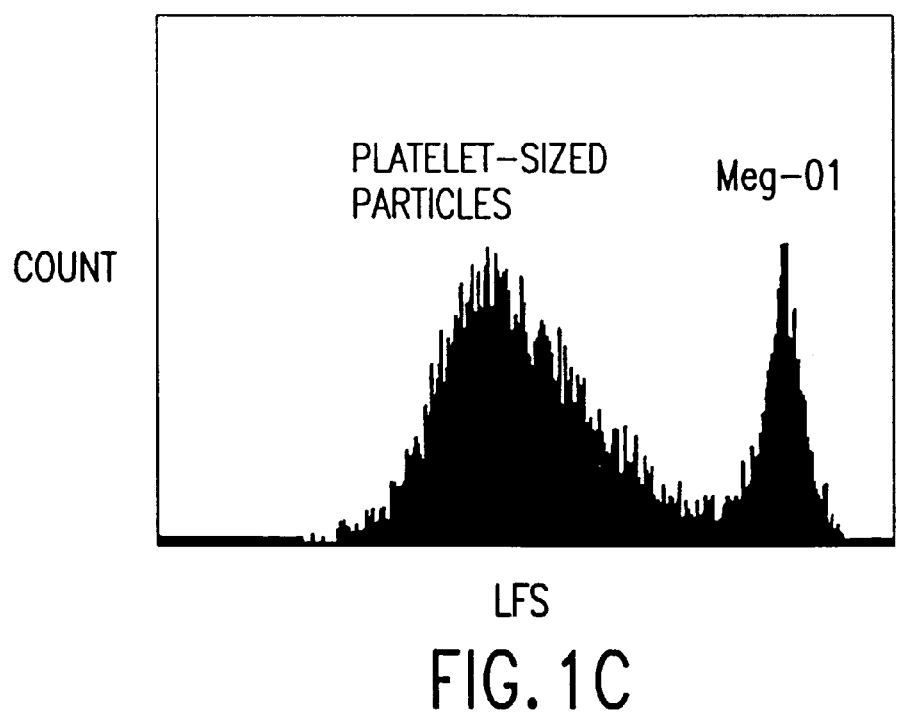

FIG. 1C shows an enhanced production of GPIIIa positive platelet-sized particles by the flow cytometric analysis of the Meg-01 cells pretreated with 100 ng/ml thrombopoietin, followed by treatment with 100 $\mu$M SNO-glu.

Figure 1D:
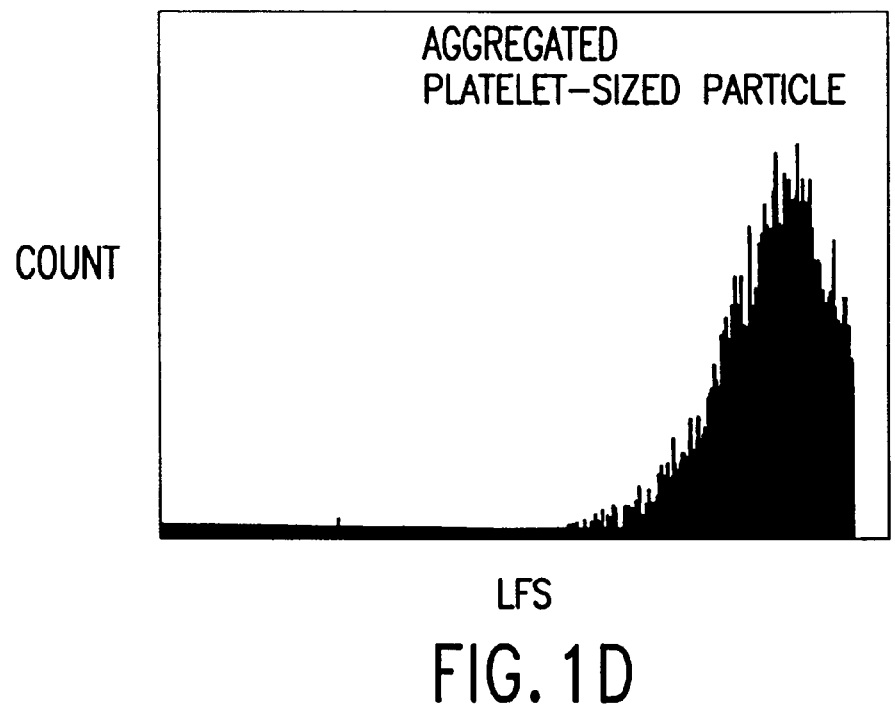

For experiments in which potential platelet aggregation was monitored, the cell suspension was centrifuged at 150 g to collect a platelet-rich fraction. The platelet-rich fraction was incubated with 10 $\mu$M thrombin-receptor activating protein (TRAP, Bachem, Torrance, Calif.), 2.5 mM $CaCl_2$, and 600 $\mu$g/ml fibrinogen (Chromogenix, Sweden). The potential platelet aggregates were then treated as described above for analysis by flow cytometry. FIG. 1D shows a shift in size of the platelet population which is suggestive of aggregate formation.

Example 2

Production of cGMP from Megakaryocytes treated with SNO-glu

The Meg-01 cells were grown as described in Example 1. The Med-01 cells, in the presence and absence of TPO, were treated with 100 μM SNO-glu for varying lengths of time. The cells were collected by centrifugation (1000 rpm for 10 minutes), and then lysed with 6% trichloroacteic acid (TCA). The cGMP was extracted with distilled water-saturated ether. The cGMP was quantified using the standard ELISA assay (Caymen Chemical Inc., Ann Arbor, Mich.). The results summarized in Table 1 show that the addition of SNO-glu results in an increased production of cGMP. This suggests that nitric oxide mediates platelet production. Interestingly, the addition of TPO during the SNO-glu treatment completely suppressed the production of cGMP.

TABLE 1

| Treatment Group | pmol cGMP/mg Protein (n = 2) |
| --- | --- |
| Untreated | 1.3 |
| 100 μM SNO-Glu, 5 minutes | 263.1 |
| 100 μM SNO-Glu, 10 minutes | 461.2 |
| 100 μM SNO-Glu, 20 minutes | 472.9 |
| 100 μM SNO-Glu, 30 minutes | 611.3 |
| 100 μM SNO-Glu in the presence of TPO, 30 minutes | 0.960 |

Example 3

Platelet Counts from iNOS(−/−) and eNOS (−/−) mice

Blood was collected from age-matched wild type (+/+), iNOS(−/−) and eNOS (−/−) mice. The blood was withdrawn from the aorta of the euthanized mice into a syringe containing 10% trisodium citrate (90 mM) to prevent coagulation and carefully placed in a tube (17 mm×199 mm) followed by centrifugation at 190 g to prepare the platelet-rich plasma. The platelets were counted using a Coulter counter, model Z (Coulter Inc., Haileah, Fla.). As summarized in Table 2, in 17-week-old knockout mice, there was a 50% decrease in platelet count in INOS (−/−) in comparison to strain- and age-matched control animals and eNOS (−/−) animals: the iNOS knockout mice (−/−) had an average platelet count of 320,000/ 1 while the wild type animals had an average platelet count of 569,000/ 1, a difference which was highly statistically significant (p=0.00325). No difference was noted between the platelet counts of the eNOS (−/−) mice and the wild type mice (564,000/ 1). These data suggest that endogenous nitric oxide is involved in thrombopoiesis.

TABLE 2

| Group | Platelet Count (/μl) | Number of Animals |
| --- | --- | --- |
| Wild Type (+/+) | 569,000 ± 400 | 7 |
| iNOS (−/−) | 320,000 ± 700 | 10 |
| eNOS (−/−) | 540,000 ± 600 | 3 |

The disclosure of each patent, patent application and publication cited or described herein is hereby incorporated by reference herein in its entirety.

Although the invention has been set forth in detail, one skilled in the art will appreciate that numerous changes and modifications can be made to the invention without departing from the spirit and scope thereof.

What is claimed is:

1. A composition comprising at least one megakaryocyte, at least one thrombopoeisis stimulating factor and at least one compound that donates, transfers, or releases nitric oxide, or induces the production of endogenous nitric oxide or endothelium-derived relaxing factor or is a substrate for nitric oxide synthase or a pharmaceutically acceptable salt thereof.

2. The composition of claim 1, wherein the compound that donates, transfers, or releases nitric oxide, or induces the production of endogenous nitric oxide or endothelium-derived relaxing factor or is a substrate for nitric oxide synthase is an S-nitrosothiol.

3. The composition of claim 2, wherein the S-nitrosothiol is S-nitroso-N-acetylcysteine, S-nitroso-captopril, S-nitroso-N-acetylpenicillamine, S-nitroso-homocysteine, S-nitroso-cysteine or S-nitroso-glutathione.

4. The composition of claim 3, wherein the S-nitrosothiol is S-nitroso-glutathione.

5. The composition of claim 2, wherein the S-nitrosothiol is:

(i) $HS(C(R_e)(R_f))_m SNO$;

(ii) $ONS(C(R_e)(R_f))_m R_e$; and (iii) $H_2N-CH(CO_2H)-(CH_2)_m-C(O)NH-CH(CH_2SNO)-C(O)NH-CH_2-CO_2H$;

wherein m is an integer from 2 to 20; $R_e$ and $R_f$ are each independently a hydrogen, an alkyl, a cycloalkoxy, a halogen, a hydroxy, an hydroxyalkyl, an alkoxyalkyl, an arylheterocyclic ring, an alkylaryl, a cycloalkylalkyl, a heterocyclicalkyl, an alkoxy, a haloalkoxy, an amino, an alkylamino, a dialkylamino, an arylamino, a diarylamino, an alkylarylamino, an alkoxyhaloalkyl, a haloalkoxy, a sulfonic acid, a sulfonic ester, an alkylsulfonic acid, an arylsulfonic acid, an arylalkoxy, an alkylthio, an arylthio, a cycloalkylthio, a cycloalkenyl, a cyano, an aminoalkyl, an aminoaryl, an aryl, an arylalkyl, an alkylaryl, a carboxamido, a alkylcarboxamido, an arylcarboxamido, an amidyl, a carboxyl, a carbamoyl, a carbamate, an alkylcarboxylic acid, an arylcarboxylic acid, an alkylcarbonyl, an arylcarbonyl, an ester, a carboxylic ester, an alkylcarboxylic ester, an arylcarboxylic ester, a haloalkoxy, a sulfonamido, an alkylsulfonamido, an arylsulfonamido, a sulfonic ester, a urea, a phosphoryl, a nitro, $-T-Q$, or $(C(R_e)(R_f))_k-T-Q$, or $R_e$ and $R_f$ taken together with the carbons to which they are attached form a carbonyl, a methanthial, a heterocyclic ring, a cycloalkyl group or a bridged cycloalkyl group; Q is $-NO$ or $-NO_2$; and T is independently a covalent bond, a carbonyl, an oxygen, $-S(O)_o-$ or $-N(R_a)R_i-$, wherein o is an integer from 0 to 2, $R_a$ is a lone pair of electrons, a hydrogen or an alkyl group; $R_i$ is a hydrogen, an alkyl, an aryl, an alkylcarboxylic acid, an aryl carboxylic acid, an alkylcarboxylic ester, an arylcarboxylic ester, an alkylcarboxamido, an arylcarboxamido, an alkylaryl, an alkylsulfinyl, an alkylsulfonyl, an arylsulfinyl, an arylsulfonyl, a sulfonamido, a carboxamido, a carboxylic ester, an amino alkyl, an amino aryl, $-CH_2-C(T-Q)(R_e)(R_f)$, or $-(N_2O_2-)^-·M^+$, wherein $M^+$ is an organic or inorganic cation; with the proviso that when $R^i$ is $-CH_2-C(T-Q)(R_e)(R_f)$ or $-(N_2O_2-)·M^+$; then "$-T-Q$" can be a hydrogen, an alkyl group, an alkoxyalkyl group, an aminoalkyl group, a hydroxy group or an aryl group.

6. The composition of claim 1, wherein the at least one compound that donates, transfers, or releases nitric oxide, or induces the production of endogenous nitric oxide or endothelium-derived relaxing factor, or is a substrate for nitric oxide synthase is:

(i) a compound that comprises at least one ON—O—, ON—N— or ON—C— group;

(ii) a compound that comprises at least one $O_2N$—O—, $O_2N$—N—, $O_2N$—S— or —$O_2N$—C— group;

(iii) a N-oxo-N-nitrosoamine having the formula: $R^1R^2$—N(O—$M^+$)—NO, wherein $R^1$ and $R^2$ are each independently a polypeptide, an amino acid, a sugar, an oligonucleotide, a straight or branched, saturated or unsaturated, aliphatic or aromatic, substituted or unsubstituted hydrocarbon, or a heterocyclic group, and $M^+$ is an organic or inorganic cation.

7. The composition of claim 6, wherein the compound comprising at least one ON—O—, ON—N— or ON—C— group is an ON—O-polypeptide, an ON—N-polypeptide, an ON—C-polypeptide, an ON—O-amino acid, an ON—N-amino acid, an ON—C-amino acid, an ON—O-sugar, an ON—N-sugar, an ON—C-sugar, an ON—O-oligonucleotide, an ON—N-oligonucleotide, an ON—C-oligonucleotide, a straight or branched, saturated or unsaturated, substituted or unsubstituted, aliphatic or aromatic ON—O-hydrocarbon, a straight or branched, saturated or unsaturated, substituted or unsubstituted, aliphatic or aromatic ON—N-hydrocarbon, a straight or branched, saturated or unsaturated, substituted or unsubstituted, aliphatic or aromatic ON—C-hydrocarbon, an ON—O-heterocyclic compound, an ON—N-heterocyclic compound or a ON—C-heterocyclic compound.

8. The composition of claim 6, wherein compound comprising at least one $O_2N$—O—, $O_2N$—N—, $O_2N$—S— or $O_2N$—C— group is an $O_2N$—O-polypeptide, an $O_2N$—N-polypeptide, an $O_2N$—S-polypeptide, an $O_2N$—C-polypeptide, an $O_2N$—O-amiino acid, $O_2N$—N-amino acid, $O_2N$—S-amino acid, an $O_2N$—C-amino acid, an $O_2N$—O-sugar, an $O_2N$—N-sugar, $O_2N$—S-sugar, an $O_2N$—C-sugar, an $O_2N$—O -oligonucleotide, an $O_2N$—N-oligonucleotide, an $O_2N$—S-oligonucleotide, an $O_2N$—C-oligonucleotide, a straight or branched, saturated or unsaturated, aliphatic or aromatic, substituted or unsubstituted $O_2N$—O-hydrocarbon, a straight or branched, saturated or unsaturated, aliphatic or aromatic, substituted or unsubstituted $O_2N$—N-hydrocarbon, a straight or branched, saturated or unsaturated, aliphatic or aromatic, substituted or unsubstituted $O_2N$—S-hydrocarbon, a straight or branched, saturated or unsaturated, aliphatic or aromatic, substituted or unsubstituted $O_2N$—C-hydrocarbon, an $O_2N$—O-heterocyclic compound, an $O_2N$—N-heterocyclic compound, an $O_2N$—S-heterocyclic compound or an $O_2N$—C-heterocyclic compound.

9. The composition of claim 1, wherein the at least one compound that donates, transfers, or releases nitric oxide, or induces the production of endogenous nitric oxide or endothelium-derived relaxing factor, or is a substrate for nitric oxide synthase, is L-arginine, L-homoarginine, N-hydroxy-L-arginine, nitrosated L-arginine, nitrosylated L-arginine, nitrosated N-hydroxy-L-arginine, nitrosylated N-hydroxy-L-arginine, citrulline, ornithine, glutamine, lysine, polypeptides comprising at least one of these amino acids or inhibitors of the enzyme arginase, cytokines, adenosin, bradykinin, calreticulin, bisacodyl, and phenolphthalein.

10. The composition of claim 1, wherein the thrombopoeisis stimulating factor is interleukin 1, interleukin 2, interleukin 3, interleukin 4, interleukin 5, interleukin 6, interleukin 7, interleukin 8, interleukin 9, interleukin 10, interleukin 11, interleukin 12, interleukin 13, interleukin 14, interleukin 15, erythropoietin, thrombopoietin, stem cell factor, flt-3 ligand, granulocyte colony stimulating factor, granulocyte macrophage colony stimulating factor, tumor growth factor beta, tumor necrosis factor alpha, interferon, fibroblast growth factor, platelet-derived growth factor, insulin-like growth factors, leukemia inhibitor factor, megakaryocyte colony stimulating factor, or mixtures thereof.

11. The composition of claim 10, wherein the thrombopoeisis stimulating factor is thrombopoietin.

12. The composition of claim 1, wherein the at least one megakaryocyte is in culture.

13. The composition of claim 12, wherein the at least one megakaryocyte in culture is obtained from a cell line, a stem cell, a tissue, bone marrow, peripheral blood, a liver, a fetal liver or a patient's own blood megakaryocytic precursors.

14. A method for producing platelets and/or proplatelets in vitro comprising adding the composition of claim 1 to at least one megakaryocyte in culture.

15. The method of claim 14, wherein the at least one megakaryocyte in culture is obtained from a cell line, a stem cell, a tissue, bone marrow, peripheral blood, a liver, a fetal liver or a patient's own blood megakaryocytic precursors.

16. A method for producing platelets and/or proplatelets in vivo in a patient in need thereof comprising administering to the patient an effective amount of the composition of claim 1.

17. A method for treating or preventing a blood platelet disorder in a patient in need thereof comprising administering to the patient a therapeutically effective amount of the composition of claim 1.

18. A method for producing platelets and/or proplatelets comprising:
   providing at least one megakaryocyte; and
   adding an effective amount of at least one thrombopoeisis stimulating factor and at least one compound that donates, transfers, or releases nitric oxide, or induces the production of endogenous nitric oxide or endothelium-derived relaxing factor or is a substrate for nitric oxide synthase or a pharmaceutically acceptable salt thereof to the at least one megakaryocyte to produce platelets and/or proplatelets.

19. The method of claim 18, wherein the megakaryocyte is in culture.

20. The method of claim 19, wherein the at least one megakaryocyte in culture is obtained from a cell line, a stem cell, a tissue, bone marrow, peripheral blood, a liver, a fetal liver or a patient's own blood megakaryocytic precursors.

21. The method of claim 18, wherein the megakaryocyte is in vivo.

22. The method of claim 18, wherein the thrombopoeisis stimulating factor is added to the at least one megakaryocyte prior to the step of adding the compound that donates, transfers, or releases nitric oxide, or induces the production of endogenous nitric oxide or endothelium-derived relaxing factor or is a substrate for nitric oxide synthase.

23. The method of claim 18, wherein the thrombopoeisis stimulating factor is interleukin 1, interleukin 2, interleukin 3, interleukin 4, interleukin 5, interleukin 6, interleukin 7, interleukin 8, interleukin 9, interleukin 10, interleukin 11, interleukin 12, interleukin 13, interleukin 14, interleukin 15, erythropoietin, thrombopoietin, stem cell factor,flt-3 ligand, granulocyte colony stimulating factor, granulocyte macrophage colony stimulating factor, tumor growth factor beta, tumor necrosis factor alpha, interferon, fibroblast growth factor, platelet-derived growth factor, insulin-like growth factors, leukemia inhibitor factor or megakaryocyte colony stimulating factor, or a mixture thereof.

24. The method of claim 23, wherein the thrombopoeisis stimulating factor is thrombopoietin.

25. The method of claim 18, wherein the compound that donates, transfers, or releases nitric oxide, or induces the production of endogenous nitric oxide or endothelium-derived relaxing factor or is a substrate for nitric oxide synthase is an S-nitrosothiol.

26. The method of claim 25, wherein the S-nitrosothiol is S-nitroso-N-acetylcysteine, S-nitroso-captopril, S-nitroso-N-acetylpenicillamine, S-nitroso-homocysteine, S-nitroso-cysteine or S-nitroso-glutathione.

27. The method of claim 26, wherein the S-nitrosothiol is S-nitroso-glutathione.

28. The method of claim 25, wherein the S-nitrosothiol is:
   (i) $HS(C(R_e)(R_f))_m SNO$;
   (ii) $ONS(C(R_e)(R_f))_m R_e$; and
   (iii) $H_2N-CH(CO_2H)-(CH_2)_m-C(O)NH-CH(CH_2SNO)-C(O)NH-CH_2-CO_2H$;
   wherein m is an integer from 2 to 20; $R_e$ and $R_f$ are each independently a hydrogen, an alkyl, a cycloalkoxy, a halogen, a hydroxy, an hydroxyalkyl, an alkoxyalkyl, an arylheterocyclic ring, an alkylaryl, a cycloalkylalkyl, a heterocyclicalkyl, an alkoxy, a haloalkoxy, an amino, an alkylamino, a dialkylamino, an arylamino, a diarylamino, an alkylarylamino, an alkoxyhaloalkyl, a haloalkoxy, a sulfonic acid, a sulfonic ester, an alkylsulfonic acid, an arylsulfonic acid, an arylalkoxy, an alkylthio, an arylthio, a cycloalkylthio, a cycloalkenyl, a cyano, an aminoalkyl, an aminoaryl, an aryl, an arylalkyl, an alkylaryl, a carboxamido, a alkylcarboxamido, an arylcarboxamido, an amidyl, a carboxyl, a carbamoyl, a carbamate, an alkylcarboxylic acid, an arylcarboxylic acid, an alkylcarbonyl, an arylcarbonyl, an ester, a carboxamide, an alkylcarboxylic ester, an arylcarboxylic ester, a haloalkoxy, a sulfonamido, an alkylsulfonamido, an arylsulfonamido, a sulfonic ester, a urea, a phosphoryl, a nitro, —T—Q , or $(C(R_e)(R_f))_k$—T—Q, or $R_e$ and $R_f$ taken together with the carbons to which they are attached form a carbonyl, a methanthial, a heterocyclic rinrg, a cycloalkyl group or a bridged cycloalkyl group; Q is —NO or —$NO_2$; and T is independently a covalent bond, a carbonyl, an oxygen, —$S(O)_o$— or —$N(R_a)R_i$—, wherein o is an integer from 0 to 2, $R_a$ is a lone pair of electrons, a hydrogen or an alkyl group; $R_i$ is a hydrogen, an alkyl, an aryl, an alkylcarboxylic acid, an aryl carboxylic acid, an alkylcarboxylic ester, an arylcarboxylic ester, an alkylcarboxamido, an arylcarboxamido, an alkylaryl, an alkylsulfinyl, an alkylsulfonyl, an arylsulfinyl, an arylsulfonyl, a sulfonamido, a carboxamido, a carboxylic ester, an amino alkyl, an amino aryl, —$CH_2$—$C(T-Q)(R_e)(R_f)$, or —$(N_2O_2-)^-·M^+$, wherein $M^+$ is an organic or inorganic cation; with the proviso that when $R_i$ is —$CH_2$—$C(T-Q)(R_e)(R_f)$ or —$(N_2O_2-)·M^+$; then "—T—Q" can be a hydrogen, an alkyl group, an alkoxyalkyl group, an aminoalkyl group, a hydroxy group or an aryl group.

29. The method of claim 18, wherein the at least one compound that donates, transfers, or releases nitric oxide, or induces the production of endogenous nitric oxide or endothelium-derived relaxing factor or is a substrate for nitric oxide synthase is:
   (i) a compound that comprises at least one ON—O—, ON—N— or ON—C— group;
   (ii) a compound that comprises at least one $O_2N$—O—, $O_2N$—N—, $O_2N$—S— or —$O_2N$—C— group;
   (iii) a N-oxo-N-nitrosoamine having the formula: $R^1R^2$—$N(O-M^+)$—NO, wherein $R^1$ and $R^2$ are each independently a polypeptide, an amino acid, a sugar, an oligonucleotide, a straight or branched, saturated or unsaturated, aliphatic or aromatic, substituted or unsubstituted hydrocarbon, or a heterocyclic group, and $M^+$ is an organic or inorganic cation.

30. The method of claim 29, wherein the compound comprising at least one ON—O—, ON—N— or ON—C— group is an ON—O-polypeptide, an ON—N-polypeptide, an ON—C-polypeptide, an ON—O-amino acid, an ON—N-amino acid, an ON—C-amino acid, an ON—O-sugar, an ON—N-sugar, an ON—C-sugar, an ON—O-oligonucleotide, an ON—N-oligonucleotide, an ON—C-oligonucleotide, a straight or branched, saturated or unsaturated, substituted or unsubstituted, aliphatic or aromatic ON—O-hydrocarbon, a straight or branched, saturated or unsaturated, substituted or unsubstituted, aliphatic or aromatic ON—N-hydrocarbon, a straight or branched, saturated or unsaturated, substituted or unsubstituted, aliphatic or aromatics ON—C-hydrocarbon, an ON—O-heterocyclic compound, an ON—N-heterocyclic compound or a ON—C-heterocyclic compound.

31. The method of claim 29, wherein compound comprising at least one $O_2N$—O—, $O_2N$—N—, $O_2N$—S— or $O_2N$—C— group is an $O_2N$—O-polypeptide, an $O_2N$—N-polypeptide, an $O_2N$—S-polypeptide, an $O_2N$—C-polypeptide, an $O_2N$—O-amino acid, $O_2N$—N-amino acid, $O_2N$—S-amino acid, an $O_2N$—C-amino acid, an $O_2N$—O-sugar, an $O_2N$—N-sugar, $O_2N$—S-sugar, an $O_2N$—C-sugar, an $O_2N$—O-oligonucleotide, an $O_2N$—N-oligonucleotide, an $O_2N$—S-oligonucleotide, an $O_2N$—C-oligonucleotide, a straight or branched, saturated or unsaturated, aliphatic or aromatic, substituted or unsubstituted $O_2N$—O-hydrocarbon, a straight or branched, saturated or unsaturated, aliphatic or aromatic, substituted or unsubstituted $O_2N$—N-hydrocarbon, a straight or branched, saturated or unsaturated, aliphatic or aromatic, substituted or unsubstituted $O_2N$—S-hydrocarbon, a straight or branched, saturated or unsaturated, aliphatic or aromatic, substituted or unsubstituted $O_2N$—C-hydrocarbon, an $O_2N$—O-heterocyclic compound, an $O_2N$—N-heterocyclic compound, an $O_2N$-S-heterocyclic compound or an $O_2N$-C-heterocyclic compound.

32. The method of claim 18, wherein the at least one compound that donates, transfers, or releases nitric oxide, or induces the production of endogenous nitric oxideor endothelium-derived relaxing factor, or is a substrate for nitric oxide synthase, is L-arginine, L-homoarginine, N-hydroxy-L-arginine, nitrosated L-arginine, nitrosylated L-arginine, nitrosated N-hydroxy-L-arginine, nitrosylated N-hydroxy-L-arginine, citrulline, ornithine, glutamine, lysine, polypeptides comprising at least one of these amino acids or inhibitors of the enzyme arginase, cytokines, adenosin, bradykinin, calreticulin, bisacodyl, and phenolphthalein.

33. The method of claim 18, further comprising adding at least one corticosteroid and/or at least one immunoglobulin.

34. The method of claim 33, wherein the corticosteroid is dexamethasone or prednisone.

35. The method of claim 33, wherein the immunoglobulin is immunoglobulin G.

36. A method for decreasing platelet counts in a patient in need thereof comprising administering to the patient a therapeutically effective amount of at least one compound that inhibits the production of the patient's nitric oxide synthesis, wherein the compound that inhibits the production of the patient's nitric oxide synthesis is $N^G$-nitro-L-arginine, $N^G$-amino-L-arginine, $N^G$—$N^G$-dimethylarginine or $N^G$-mono-methyl-L-arginine, or mixtures thereof.

27

37. A composition comprising at least one thrombopoeisis stimulating factor and at least one compound that donates, transfers, or releases nitric oxide, or induces the production of endogenous nitric oxide or endothelium-derived relaxing factor or is a substrate for nitric oxide synthase.

38. The composition of claim 37, wherein the thrombopoeisis stimulating factor is interleukin 1, interleukin 2, interleukin 3, interleukin 4, interleukin 5, interleukin 6, interleukin 7, interleukin 8, interleukin 9, interleukin 10, interleukin 11, interleukin 12, interleukin 13, interleukin 14, interleukin 15, erythropoietin, thrombopoietin, stem cell factor, flt-3 ligand, granulocyte colony stimulating factor, granulocyte macrophage colony stimulating factor, tumor growth factor beta, tumor necrosis factor alpha, interferon, fibroblast growth factor, platelet-derived growth factor, insulin-like growth factors, leukemia inhibitor factor or megakaryocyte colony stimulating factor, or mixtures thereof.

39. The composition of claim 38, wherein the thrombopoeisis stimulating factor is thrombopoietin.

40. The composition of claim 37, wherein the compound that donates, transfers, or releases nitric oxide, or induces the production of endogenous nitric oxide or endothelium-derived relaxing factor or is a substrate for nitric oxide synthase is an S-nitrosothiol.

41. The composition of claim 40, wherein the S-nitrosothiol is S-nitroso-N-acetylcysteine, S-nitroso-captopril, S-nitroso-N-acetylpenicillamine, S-nitroso-homocysteine, S-nitroso-cysteine or S-nitroso-glutathione.

42. The composition of claim 41, wherein the S-nitrosothiol is S-nitroso-glutathione.

43. The composition of claim 40, wherein the S-nitrosothiol is:
(i) $HS(C(R_e)(R_f))_m SNO$;
(ii) $ONS(C(R_e)(R_f))_m R_e$; and
(iii) $H_2N$—$CH(CO_2H)$—$(CH_2)_m$—$C(O)NH$—$CH(CH_2SNO)$—$C(O)NH$—$CH_2$—$CO_2H$;

wherein m is an integer from 2 to 20; $R_e$ and $R_f$ are each independently a hydrogen, an alkyl, a cycloalkoxy, a halogen, a hydroxy, an hydroxyalkyl, an alkoxyalkyl, an arylheterocyclic ring, an alkylaryl, a cycloalkylalkyl, a heterocyclicalkyl, an alkoxy, a haloalkoxy, an amino, an alkylamino, a dialkylamino, an arylamino, a diarylamino, an alkylarylamino, an alkoxyhaloalkyl, a haloalkoxy, a sulfonic acid, a sulfonic ester, an alkylsulfonic acid, an arylsulfdnic acid, an arylalkoxy, an alkylthio, an arylthio, a cycloalkylthio, a cycloalkenyl, a cyano, an aminoalkyl, an aminoaryl, an aryl, an arylalkyl, an alkylaryl, a carboxamido, a alkylcarboxamido, an arylcarboxamido, an amidyl, a carboxyl, a carbamoyl, a carbamate, an alkylcarboxylic acid, an arylcarboxylic acid, an alkylcarbonyl, an arylcarbonyl, an ester, a carboxylic ester, an alkylcarboxylic ester, an arylcarboxylic ester, a haloalkoxy, a sulfonamido, an alkylsulfonamido, an arylsulfonamido, a sulfonic ester, a urea, a phosphoryl, a nitro, —T—Q , or $(C(R_e)(R_f))_k$—T—Q, or $R_e$ and $R_f$ taken together with the carbons to which they are attached form a carbonyl, a methanthial, a heterocyclic ring, a cycloalkyl group or a bridged cycloalkyl group; Q is —NO or —$NO_2$; and T is independently a covalent bond, a carbonyl, an oxygen, —S(O)$_o$— or —N($R_a$)$R_i$—, wherein o is an integer from 0 to 2, $R_a$ is a lone pair of electrons, a hydrogen or an alkyl group; $R_i$ is a hydrogen, an alkyl, an aryl, an alkylcarboxylic acid, an aryl carboxylic acid, an alkylcarboxylic ester, an arylcarboxylic ester,

28 an alkylcarboxamido, an arylcarboxamido, an alkylaryl, an alkylsulfinyl, an alkylsulfonyl, an arylsulfinyl, an arylsulfonyl, a sulfonamido, a carboxamido, a carboxylic ester, an amino alkyl, an amino aryl, —$CH_2$—$C(T$—$Q)(R_e)(R_f)$, or —$(N_2O_2$-$)^-·M^+$, wherein $M^+$ is an organic or inorganic cation; with the proviso that when $R_i$ is —$CH_2$—$C(T$—$Q)(R_e)(R_f)$ or —$(N_2O_2$-$)·M^+$; then "—T—Q" can be a hydrogen, an alkyl group, an alkoxyalkyl group, an aminoalkyl group, a hydroxy group or an aryl group.

44. The composition of claim 37, wherein the at least one compound that donates, transfers, or releases nitric oxide, or induces the production of endogenous nitric oxide or endothelium-derived relaxing factor, or is a substrate for nitric oxide synthase is:
(i) a compound that comprises at least one ON—O—, ON—N— or ON—C— group;
(ii) a compound that comprises at least one $O_2N$—O—, $O_2N$—N—, $O_2N$—S— or —$O_2N$—C— group;
(iii) a N-oxo-N-nitrosoamine having the formula: $R^1R_2$—$N(O$—$M^+)$—$NO$, wherein $R^1$ and $R^2$ are each independently a polypeptide, an amino acid, a sugar, an oligonucleotide, a straight or branched, saturated or unsaturated, aliphatic or aromatic, substituted or unsubstituted hydrocarbon, or a heterocyclic group, and $M^+$ is an organic or inorganic cation.

45. The composition of claim 44, wherein the compound comprising at least one ON—O—, ON—N— or ON—C— group is an ON—O-polypeptide, an ON—N-polypeptide, an ON—C-polypeptide, an ON—O-amino acid, an ON—N-amino acid, an ON—C-amino acid, an ON—O-sugar, an ON—N-sugar, an ON—C-sugar, an ON—O-oligonucleotide, an ON—N-oligonucleotide, an ON—C-oligonucleotide, a straight or branched, saturated or unsaturated, substituted or unsubstituted, aliphatic or aromatic ON—O-hydrocarbon, a straight or branched, saturated or unsaturated, substituted or unsubstituted, aliphatic or aromatic ON—N-hydrocarbon, a straight or branched, saturated or unsaturated, substituted or unsubstituted, aliphatic or aromatic ON—C-hydrocarbon, an ON—O-heterocyclic compound, an ON—N-heterocyclic compound or a ON—C-heterocyclic compound.

46. The composition of claim 44, wherein compound comprising at least one $O_2N$—O—, $O_2N$—N—, $O_2N$—S— or $O_2N$—C— group is an $O_2N$—O-polypeptide, an $O_2N$—N-polypeptide, an $O_2N$—S-polypeptide, an $O_2N$—C-polypeptide, an $O_2N$—O-amino acid, $O_2N$—N-amino acid, $O_2N$—S-amino acid, an $O_2N$—C-amino acid, an $O_2N$—O-sugar, an $O_2N$—N-sugar, $O_2N$—S-sugar, an $O_2N$—C-sugar, an $O_2N$—O-oligonucleotide, an $O_2N$—N-oligonucleotide, an $O_2N$—S-oligonucleotide, an $O_2N$—C-oligonucleotide, a straight or branched, saturated or unsaturated, aliphatic or aromatic, substituted or unsubstituted $O_2N$—O-hydrocarbon, a straight or branched, saturated or unsaturated, aliphatic or aromatic, substituted or unsubstituted $O_2N$—N-hydrocarbon, a straight or branched, saturated or unsaturated, aliphatic or aromatic, substituted or unsubstituted $O_2N$—S-hydrocarbon, a straight or branched, saturated or unsaturated, aliphatic or aromatic, substituted or unsubstituted $O_2N$—C-hydrocarbon, an $O_2N$—O-heterocyclic compound, an $O_2N$—N-heterocyclic compound, an $O_2N$—S-heterocyclic compound or an $O_2N$—C-heterocyclic compound.

47. The composition of claim 37, wherein the at least one compound that donates, transfers, or releases nitric oxide, or induces the production of endogenous nitric oxide or endothelium-derived relaxing factor, or is a substrate for nitric oxide synthase, is L-arginine, L-homoarginine, N-hydroxy-L-arginine, nitrosated L-arginine, nitrosylated L-arginine, nitrosated N-hydroxy-L-arginine, nitrosylated N-hydroxy-L-arginine, citrulline, ornithine, glutamine, lysine, polypeptides comprising at least one of these amino acids or inhibitors of the enzyme arginase, cytokines, adenosin, bradykinin, calreticulin, bisacodyl, and phenolphthalein.

48. A method for producing platelets and/or proplatelets in vitro comprising adding the composition of claim 37 to at least one megakaryocyte in culture.

49. The method of claim 48, wherein the at least one megakaryocyte in culture is obtained from a cell line, a stem cell, a tissue, bone marrow, peripheral blood, a liver, a fetal liver or a patient's own blood megakaryocytic precursors.

50. A method for producing platelets and/or proplatelets in vivo in a patient in need thereof comprising administering to the patient an effective amount of the composition of claim 37.

51. A method for treating or preventing a blood platelet disorder in a patient in need thereof comprising administering to the patient a therapeutically effective amount of the composition of claim 37.

52. A method for treating or preventing a blood platelet disorder in a patient in need thereof comprising administering to the patient a therapeutically effective amount of at least one thrombopoeisis stimulating factor and at least one compound that donates, transfers, or releases nitric oxide, or induces the production of endogenous nitric oxide or endothelium-derived relaxing factor or is a substrate for nitric oxide synthase.

53. The method of claim 52, wherein the compound is administered orally or by injection.

54. A method for treating or preventing a blood platelet disorder in a patient in need thereof comprising:
providing at least one megakaryocyte in culture;
adding at least one thrombopoeisis stimulating factor and at least one compound that donates, transfers, or releases nitric oxide, or induces the production of endogenous nitric oxide or endothelium-derived relaxing factor or is a substrate for nitric oxide synthase to the at least one megakaryocyte in culture to produce platelets and/or proplatelets; and
administering a therapeutically effective amount of the platelets and/or proplatelets to the patient.

55. The method of claim 54, wherein the thrombopoeisis stimulating factor is added to the at least one megakaryocyte prior to the step of adding the compound that donates, transfers, or releases nitric oxide, or induces the production of endogenous nitric oxide or endothelium-derived relaxing factor or is a substrate for nitric oxide synthase.

56. The method of claim 54, wherein the at least one megakaryocyte in culture is obtained from a cell line, a stem cell, a tissue, bone marrow, peripheral blood, a liver, a fetal liver or a patient's own blood megakaryocytic precursors.

57. The method of claimed 54, wherein the platelets and/or proplatelets are administered orally or by injection.

58. The method of claim 17, 51, 52 or 54, wherein the blood disorder is thrombc ytopenia, thrombocythmia or thrombocytopathy.

59. The method of claim 17 or 51, wherein the composition is administered orally or by injection.

60. A composition comprising at least one megakaryocyte in culture and at least one compound that donates, transfers, or releases nitric oxide, or induces the production of endogenous nitric oxide or endothelium-derived relaxing factor or is a substrate for nitric oxide synthase or a pharmaceutically acceptable salt thereof.

61. The composition of claim 60, wherein the compound that donates, transfers, or releases nitric oxide, or induces the production of endogenous nitric oxide or endothelium-derived relaxing factor or is a substrate for nitric oxide synthase is an S-nitrosothiol.

62. The composition of claim 61, wherein the S-nitrosothiol is S-nitroso-N-acetylcysteine, S-nitroso-captopril, S-nitroso-N-acetylpenicillamine, S-nitroso-homocysteine, S-nitroso-cysteine or S-nitroso-glutathione.

63. The composition of claim 62, wherein the S-nitrosothiol is S-nitroso-glutathione.

64. The composition of claim 61, wherein the S-nitrosothiol is:
(i) $HS(C(R_e)(R_f))_m SNO$;
(ii) $ONS(C(R_e)(R_f))_m R_e$; and
(iii) $H_2N-CH(CO_2H)-(CH_2)_m-C(O)NH-CH(CH_2SNO)-C(O)NH-CH_2-CO_2H$;
wherein m is an integer from 2 to 20; $R_e$ and $R_f$ are each independently a hydrogen, an alkyl, a cycloalkoxy, a halogen, a hydroxy, an hydroxyalkyl, an alkoxyalkyl, an arylheterocyclic ring, an alkylaryl, a cycloalkylalkyl, a heterocyclicalkyl, an alkoxy, a haloalkoxy, an amino, an alkylamino, a dialkylamino, an arylamino, a diarylamino, an alkylarylamino, an alkoxyhaloalkyl, a haloalkoxy, a sulfonic acid, a sulfonic ester, an alkylsulfonic acid, an arylsulfonic acid, an. arylalkoxy, an alkylthio, an arylthio, a cycloalkylthio, a cycloalkenyl, a cyano, an aminoalkyl, an aminoaryl, an aryl, an arylalkyl, an alkylaryl, a carboxamido, a alkylcarboxamido, an arylcarboxamido, an amidyl, a carboxyl, a carbamoyl, a carbamate, an alkylcarboxylic acid, an arylcarboxylic acid, an alkylcarbonyl, an arylcarbonyl, an ester, a carboxylic ester, an alkylcarboxylic ester, an arylcarboxylic ester, a haloalkoxy, a sulfonamido, an alkylsulfonamido, an arylsulfonamido, a sulfonic ester, a urea, a phosphoryl, a nitro, $-T-Q$, or $(C(R_e)(R_f))_k-T-Q$, or $R_e$ and $R_f$ taken together with the carbons to which they are attached form a carbonyl, a methanthial, a heterocyclic ring, a cycloalkyl group or a bridged cycloalkyl group; Q is $-NO$ or $-NO_2$; and T is independently a covalent bond, a carbonyl, an oxygen, $-S(O)_o-$ or $-N(R_a)R_i-$, wherein o is an integer from 0 to 2, $R_a$ is a lone pair of electrons, a hydrogen or an alkyl group; $R_i$ is a hydrogen, an alkyl, an aryl, an alkylcarboxylic acid, an aryl carboxylic acid, an alkylcarboxylic ester, an arylcarboxylic ester, an alkylcarboxamido, an arylcarboxamido, an alkylaryl, an alkylsulfinyl, an alkylsulfonyl, an arylsulfinyl, an arylsulfonyl, a sulfonamido, a carboxamido, a carboxylic ester, an amino alkyl, an amino aryl, $-CH_2-C(T-Q)(R_e)(R_f)$, or $-(N_2O_2-)^- \cdot M^+$, wherein $M^+$ is an organic or inorganic cation; with the proviso that when $R_i$ is $-CH_2-C(T-Q)(R_e)(R_f)$ or $-(N_2O_2-)\cdot M^+$; then "$-T-Q$" can be a hydrogen, an alkyl group, an alkoxyalkyl group, an aminoalkyl group, a hydroxy group or an aryl. group.

65. The composition of claim 60, wherein the at least one compound that donates, transfers, or releases nitric oxide, or induces the production of endogenous nitric oxide or endothelium-derived relaxing factor, or is a substrate for nitric oxide synthase is:
(i) a compound that comprises at least one ON—O—, ON—N— or ON—C— group;
(ii) a compound that comprises at least one $O_2N$—O—, $O_2N$—N—, $O_2N$—S— or —$O_2N$—C— group;

(iii) a N-oxo-N-nitrosoamine having the formula: $R^1R^2$—N(O—$M^+$)—NO, wherein $R^1$ and $R^2$ are each independently a polypeptide, an amino acid, a sugar, an oligonucleotide, a straight or branched, saturated or unsaturated, aliphatic or aromatic, substituted or unsubstituted hydrocarbon, or a heterocyclic group, and $M^+$ is an organic or inorganic cation.

66. The composition of claim 65, wherein the compound comprising at least one ON—O—, ON—N— or ON—C— group is an ON—O-polypeptide, an ON—N-polypeptide, an ON—C-polypeptide, an ON—O-amino acid, an ON—N-amino acid, an ON—C-amino acid, an ON—O-sugar, an ON—N-sugar, an ON—C-sugar, an ON—O-oligonucleotide, an ON—N-oligonucleotide, an ON—C-oligonucleotide, a straight or branched, saturated or unsaturated, substituted or unsubstituted, aliphatic or aromatic ON—O-hydrocarbon, a straight or branched, saturated or unsaturated, substituted or unsubstituted, aliphatic or aromatic ON—N-hydrocarbon, a straight or branched, saturated or unsaturated, substituted or unsubstituted, aliphatic or aromatic ON—C-hydrocarbon, an ON—O-heterocyclic compound, an ON—N-heterocyclic compound or a ON—C-heterocyclic compound.

67. The composition of claim 65, wherein compound comprising at least one $O_2N$—O—, $O_2N$—N—, $O_2N$—S— or $O_2N$—C— group is an $O_2N$—O-polypeptide, an $O_2N$—N-polypeptide, an $O_2N$—S-polypeptide, an $O_2N$—C-polypeptide, an $O_2N$—O-amino acid, $O_2N$—N-amino acid, $O_2N$—S-amino acid, an $O_2N$—C-amino acid, an $O_2N$—O-sugar, an $O_2N$—N-sugar, $O_2N$-S-sugar, an $O_2N$—C-sugar, an $O_2N$—O-oligonucleotide, an $O_2N$—N-oligonucleotide, an $O_2N$—S-oligonucleotide, an $O_2N$—C-oligonucleotide, a straight or branched, saturated or unsaturated, aliphatic or aromatic, substituted or unsubstituted $O_2N$—O-hydrocarbon, a straight or branched, saturated or unsaturated, aliphatic or aromatic, substituted or unsubstituted $O_2N$—N-hydrocarbon, a straight or branched, saturated or unsaturated, aliphatic or aromatic, substituted or unsubstituted $O_2N$—S-hydrocarbon, a straight or branched, saturated or unsaturated, aliphatic or aromatic, substituted or unsubstituted $O_2N$—C-hydrocarbon, an $O_2N$—O-heterocyclic compound, an $O_2N$—N-heterocyclic compound, an $O_2N$—S-heterocyclic compound or an $O_2N$—C-heterocyclic compound.

68. The composition of claim 60, wherein the at least one compound that donates, transfers, or releases nitric oxide, or induces the production of endogenous nitric oxide or endothelium-derived relaxing factor, or is a substrate for nitric oxide synthase, is L-arginine, L-homoarginine, N-hydroxy-L-arginine, nitrosated L-arginine, nitrosylated L-arginine, nitrosated N-hydroxy-L-arginine, nitrosylated N-hydroxy-L-arginine, citrulline, ornithine, glutamine, lysine, polypeptides comprising at least one of these amino acids or inhibitors of the enzyme arginase, cytokines, adenosin, bradykinin, calreticulin, bisacodyl, and phenolphthalein.

69. The composition of claim 60, wherein the at least one megakaryocyte in culture is obtained from a cell line, a stem cell, a tissue, bone marrow, peripheral blood, a liver, a fetal liver or a patient's own blood megakaryocytic precursors.

70. A method for producing platelets and/or proplatelets in vitro comprising adding the composition of claim 60 to at least one megakaryocyte in culture.

71. The method of claim 70, wherein the at least one megakaryocyte in culture is obtained from a cell line, a stem cell, a tissue, bone marrow, peripheral blood, a liver, a fetal liver or apatient's own blood megakaryocytic precursors.

72. A method for producing platelets and/or proplatelets in vivo in a patient in need thereof comprising administering to the patient an effective amount of the composition of claim 60.

73. A method for treating or preventing a blood platelet disorder in a patient in need thereof comprising administering to the patient a therapeutically effective amount of the composition of claim 60.

74. The method of claim 73, wherein the blood disorder is thrombocytopenia, thrombocythmia or thrombocytopathy.

75. The miethod of claim 73, wherein the composition is administered orally or by injection.

76. The composition of claim 60, further comprising at least one thrombopoeisis stimulating factor.

77. The composition of claim 76, wherein the thrombopoeisis stimulating factor is interleukin 1, interleukin 2, interleukin 3, interleukin 4, interleukin 5, interleukin 6, interleukin 7, interleukin 8, interleukin 9, interleukin 10, interleukin 11, interleukin 12, interleukin 13, interleukin 14, interleukin 15, erythropoietin, thrombopoietin, stem cell factor, flt-3 ligand, granulocyte colony stimulating factor, granulocyte macrophage colony stimulating factor, tumor growth factor beta, tumor necrosis factor alpha, interferon, fibroblast growth factor, platelet-derived growth factor, insulin-like growth factors, leukemia inhibitor factor, megakaryocyte colony stimulating factor, or mixtures thereof.

78. The composition of claim 77, wherein the thrombopoeisis stimulating factor is thrombopoietin.

79. A method for producing platelets and/or proplatelets in vitro comprising adding the composition of claim 76 to at least one megakaryocyte in culture.

80. The method of claim 79, wherein the at least one megakaryocyte in culture is obtained from a cell line, a stem cell, a tissue, bone marrow, peripheral blood, a liver, a fetal liver or a patient's own blood megakaryocytic precursors.

81. A method for producing platelets and/or proplatelets in vivo in a patient in need thereof comprising administering to the patient an effective amount of the composition of claim 76.

82. A method for treating or preventing a blood platelet disorder in a patient in need thereof comprising administering to the patient a therapeutically effective amount of the composition of claim 76.

83. The method of claim 82, wherein the blood disorder is thrombocytopenia, thrombocythmia or thrombocytopathy.

* * * * *